US007388081B2

(12) United States Patent
Seki et al.

(10) Patent No.: US 7,388,081 B2
(45) Date of Patent: Jun. 17, 2008

(54) METHOD FOR MANUFACTURING GLYCOPROTEINS HAVING HUMAN-TYPE GLYCOSYLATION

(75) Inventors: Tatsuji Seki, Osaka (JP); Kazuhito Fujiyama, Osaka (JP)

(73) Assignee: DFB Biotech, Inc., Fort Worth, TX (US)

( * ) Notice: Subject to any disclaimer, the term of this patent is extended or adjusted under 35 U.S.C. 154(b) by 276 days.

(21) Appl. No.: 10/870,635

(22) Filed: Jun. 17, 2004

(65) Prior Publication Data
US 2005/0143564 A1 Jun. 30, 2005

Related U.S. Application Data

(62) Division of application No. 09/857,651, filed as application No. PCT/JP99/06881 on Dec. 8, 1999, now Pat. No. 6,998,267.

(30) Foreign Application Priority Data
Dec. 9, 1998 (JP) ................... 10-350584

(51) Int. Cl.
C07K 1/00 (2006.01)
C12N 5/04 (2006.01)
A01H 1/00 (2006.01)
(52) U.S. Cl. ................ 530/395; 530/397; 435/419; 435/430; 435/468; 800/278; 800/288; 800/298
(58) Field of Classification Search ............ 530/395, 530/397; 435/419, 430, 468; 800/288, 298, 800/278
See application file for complete search history.

(56) References Cited

U.S. PATENT DOCUMENTS

| | | | |
|---|---|---|---|
| 5,202,422 A | 4/1993 | Hiatt et al. | |
| 5,879,912 A | 3/1999 | Roth | |
| 5,959,177 A | 9/1999 | Hein et al. | 800/288 |
| 6,046,040 A | 4/2000 | Nishiguchi et al. | |
| 6,054,304 A | 4/2000 | Taniguchi et al. | |
| 6,331,418 B1 | 12/2001 | Roth | |
| 6,388,068 B1 | 5/2002 | Satoh et al. | |
| 6,602,684 B1 | 8/2003 | Umana et al. | 435/69.1 |

(Continued)

FOREIGN PATENT DOCUMENTS

DE  19754622  6/1999

(Continued)

OTHER PUBLICATIONS

Palacpac, Nirianne et al., "Stable Expression of human β1, 4-galactosyltransferase in plant cells modifies N-linked glycosylation patterns", Proc. Natl. Acad. Sci. USA, vol. 96, pp. 4692-4697, Apr. 1999 Plant Biology.

(Continued)

*Primary Examiner*—Jon Weber
*Assistant Examiner*—Rita Mitra
(74) *Attorney, Agent, or Firm*—Wolf, Greenfield & Sacks, P.C.

(57) ABSTRACT

The present invention provides a method for manufacturing a glycoprotein having a human-type sugar chain comprising a step in which transformed plant cell is obtained by introducing to a plant cell the gene of glycosyltransfetase and the gene of an exogenous glycoprotein, and a step in which the obtained transformed plant cell is cultivated.

13 Claims, 21 Drawing Sheets

U.S. PATENT DOCUMENTS

| | | |
|---|---|---|
| 6,653,459 B1 | 11/2003 | Von Schaewen ............ 536/23.1 |
| 6,998,267 B1 | 2/2006 | Seki et al. |
| 2001/0055584 A1 | 12/2001 | McKenzie et al. |
| 2002/0174453 A1 | 11/2002 | Daniells et al. |
| 2004/0072290 A1 | 4/2004 | Umana et al. |
| 2004/0181827 A1 | 9/2004 | Schaewen |
| 2004/0214273 A1 | 10/2004 | Fujiyama et al. |
| 2005/0143564 A1 | 6/2005 | Seki et al. |
| 2005/0144670 A1 | 6/2005 | Fujiyama et al. |
| 2005/0223430 A1 | 10/2005 | Bakker et al. |
| 2006/0253928 A1 | 11/2006 | Bakker et al. |
| 2007/0089201 A1 | 4/2007 | Briggs et al. |
| 2007/0214519 A1 | 9/2007 | Fujiyama et al. |

FOREIGN PATENT DOCUMENTS

| | | |
|---|---|---|
| EP | 0 351 313 A2 | 1/1990 |
| EP | 0 550 756 A1 | 7/1993 |
| EP | 0 737 745 A1 | 10/1996 |
| EP | 1 243 647 A1 | 9/2002 |
| JP | 99/006881 | 5/2000 |
| JP | 1999/06881 | 5/2000 |
| JP | 200287692 | 10/2000 |
| JP | 99/006881 | 3/2001 |
| JP | 1999/06881 | 3/2001 |
| JP | 02/002091 | 1/2003 |
| JP | 02/000361 | 2/2003 |
| JP | 02/000361 | 7/2003 |
| JP | 02/002091 | 7/2003 |
| NL | 00/000775 | 3/2001 |
| NL | 00/000775 | 1/2002 |
| US | 03/037905 | 4/2006 |
| WO | 92/18537 | 10/1992 |
| WO | 94/12646 | 6/1994 |
| WO | 95/02683 | 1/1995 |
| WO | 97/04122 | 2/1997 |
| WO | 98/31826 | 7/1998 |
| WO | 9831828 | 7/1998 |
| WO | 99/24584 | 5/1999 |
| WO | 9929879 | 6/1999 |
| WO | 99/38987 | 8/1999 |
| WO | 99/38990 | 8/1999 |
| WO | 99/51185 | 10/1999 |
| WO | 00/29603 | 5/2000 |
| WO | 0028792 | 5/2000 |
| WO | 00/34490 | 6/2000 |
| WO | 00/49153 | 8/2000 |
| WO | 00/52136 | 9/2000 |
| WO | 00/287692 | 10/2000 |
| WO | 01/29242 | 4/2001 |
| WO | 01/31044 | 5/2001 |
| WO | 01/31045 | 5/2001 |
| WO | 01/49831 A2 | 7/2001 |
| WO | 01/49831 A3 | 7/2001 |
| WO | 0149821 | 7/2001 |
| WO | 01/62912 A2 | 8/2001 |
| WO | 0162912 | 8/2001 |
| WO | 01/64901 A1 | 9/2001 |
| WO | 01/81591 A1 | 11/2001 |
| WO | 01/82912 | 11/2001 |
| WO | 02/00879 | 1/2002 |
| WO | 0257468 | 7/2002 |
| WO | 02/070672 A2 | 9/2002 |
| WO | 02/070672 A3 | 9/2002 |
| WO | 03/011878 A2 | 2/2003 |
| WO | 03/011878 A3 | 2/2003 |
| WO | 03/078614 A2 | 9/2003 |
| WO | 03/078614 A3 | 9/2003 |
| WO | 03/078637 | 9/2003 |
| WO | 03076614 | 9/2003 |
| WO | 04/050838 | 6/2004 |

OTHER PUBLICATIONS

Takahashi et al., Biochemistry 1986, 25:388-395.

Dinter and Berger 1995, The regulation of cell and tissue specific expression of glycans by glycosyltransferases, in Glycoimmunology, Alavi and Axford (eds), Plenum Press, New York, pp. 53-82.

Sakai, Hiromi et al., "Human glycosyltransferase expression and intracellular/intercellular glycoprotein sugar chain structure in cultured tobacco BY2 cells. (Abstract)" IC Botech, Osaka, Nara Institute of Science and Technology, Mar. 5, 1998.

Yoshida, Shohei et al., Expression of β1, 4-Galactosyltransferase in Tobacco Culture Cell, Sep. 15, 1995.

Zhang, Yi, et al. Transformation of Tobacco Using Human β-1,4-galactosyltransferase Gene and Regeneration of Transgenic Plants. Annual Reports of IC Biotech, vol. 18, 1995, publicly available Aug. 31, 1998.

Bakker H et al: "Galactose-Extended Glycans Of Antibodies Produced By Transgenic Plants", Proceedings Of The National Academy Of Sciences Of USA, National Academy Of Science. Washington, US, vol. 98, No. 5, Feb. 27, 2001, pp. 2899-2904.

Bakker Hans et al: "An *Arabidopsis thaliana* cDNA Complements The N-Acetylglucosaminyltransferase I Deficiency Of CHO Lec1 Cells", Biochemical And Biophysical Research Communications, vol. 261, No. 3, Aug. 11, 1999, pp. 829-832.

Cabanes-Macheteau Marion et al: "N-Glycosylation Of A Mouse IgG Expressed In Transgenic Tobacco Plants." Glycobioloby, vol. 9, No. 4, Apr. 1999, pp. 365-372.

Choi, Byung-Kwon et al.: Use Of Combinatorial Genetic Libraries To Humanize N-Linked Glycosylation In The Yeast Pichia Pastoris, Apr. 29, 2003, Pnas vol. 100, No. 9, pp. 4022-4027.

Database EMBL 'Online! Apr. 28, 2000 Retrieved From Ebi Database Accession No. Aj 277603, Sequence, Annotation, Bakker, H "*Arabidopsis thaliana* mRNA for Beta1,2-Xylosylftransferase (xylt gene)".

Elbers Ingrid J W et al: "Influence Of Growth Conditions And Developmental Stage On N-Glycan Heterogeneity Of Transgenic Immunoglobulin G And Endogenous Proteins In Tobacco Leaves", Plant Physiology (Rockville), vol. 126, No. 3, Jul. 2001, pp. 1314-1322.

Essl D et al: "The N-Terminal 77 Amino Acids From Tobacco N-Acetylglucosaminyltransferase I Are Sufficient To Retain A Reporter Protein In The Golgi Apparatus Of *Nicotiana benthamiana* Cells" Febs Letters, Elsevier Science Publishers, Amsterdam, NI, vol. 453, No. 1-2, Jun. 18, 1999, pp. 169-173.

Fujiyama Kazuhito et al: "In Vivo Conversion Of Glycan To Human Compatible Type By Transformed Tobacco Cells." Biochemical And Biophysical Research Communications, vol. 289, No. 2, Nov. 30, 2001, pp. 553-557.

Gasser, Charles S. et al.: Genetically Engineering Plants for Crop Improvement; Science vol. 244, Jun. 16, 1989, p. 1293-1299.

Gomez L And Chrispeels M J: "Complementation Of An *Arabidopsis thaliana* Mutant That Lacks Complex Asparagine-Linked Gylcans With The Human cDNA Encoding N-acetylglucosaminyltransferase I", Proceedings Of The National Academy Of Sciences Of USA, National Academy Of Science. Washington, US, vol. 91, Mar. 1994, pp. 1829-1833.

Grabenhorst Eckart et al: "The Cytoplasmic, Transmembrane, And Stem Regions Of Glycosyltransferases Specify Their In Vivo Functional Sublocalization And Stability In The Golgi", Journal Of Biological Chemistry, vol. 274, No. 51, Dec. 17, 1999, pp. 36107-36116.

Hamilton, Stephen R. et al., Production Of Complex Human Glycoproteins In Yeast, Aug. 29, 2003, Science, vol. 302, pp. 1244-1246.

Hiei Y et al. "Experimental Protocols for Model Plants: Rice and Arabidopsis version" Plant J. 6: 271-282 (1994) (Original version copy and translation).

Hiei Y et al. "Transformation of Rice Medicated by *Agrobacterium tumefaciens*" Plant molecular biology 35: 205-218, 1997 Printed in Belgium.

Hess, Dieter et al.: Tranformation experiments by pipetting Agrobacterium into the spikelets of wheat (*Triticm aestivum* L.) Plant Science 72 (1990) 233-244, Elsevier Scientific Publishers of Ireland Ltd. Printed and published in Ireland.

Hollister, Jason et al, "Engineering The Protein N-Glycosylation Pathway In Insect Cells For Production Of Biantennary Complex N-Glycans.", Biochemistry, vol. 41, No. 50, Dec. 17, 2002, pp. 15093-15104.

Ihara Y et al. "cDNA Cloning, Expression, And Chromosomal Localization Of Human N-acetylglucosaminyltransferase III (GnT-III)" Journal Of Biochemistry, vol. 113, No. 6, 1993, pp. 692-698.

Ishida, Y et al: "High Efficiency Transformation of Maize (*Zea mays* L.) mediated by *Agrobacterium umefaciens*" Nature Biotechnology vol. 14, Jun. 1996, pp. 745-750.

Jähne, A et al.: "Genetic Engineering of Ceral crop Plants: A Review", Euphyica 85535-44, 1995 Kluwer Academic Publishers, printed in the Neatherlands.

Jenkins N. et al.: "Getting The Glycosylation Right: Implications For The Biotechnology Industry", Nat Biotechnol Aug. 14, 1996; 14(8):975-81.

Kawar Ziad et al: "Insect Cells Encode A Class II Alpha-Mannosidase With Unique Properties", Journal Of Biological Chemistry, vol. 267, No. 19, May 11, 2001, pp. 16335-16340.

Kieliszewski et al.: "Tandem Mass Sepctrometry and Structural Eludcidation of Glycopeptides from Hydroxproline-rich Plant Cell Wall Glycoprotein Indicate that Contiguous Hytdroxyproline Residues are the Majore Sites of Hydroxyproline O-Arabinosylation" The Journal of Biological Chemistry, vol. 270, No. 6, Issue of Feb. 10, pp. 2591-2549, 1995 Printed U.S.A.

Kleene R et al: "Expression Of Soluble Active Human Beta1, 4 Galactosyltransferase In *Saccharomyces cerevisiae*", Biochemical And Biophysical Research Communications, Us, Adademic Press, Inc., Orlando, Fl., vol. 201, No. 1, May 30, 1994, pp. 160-167.

Ku, Maurice S.B. et al: "High-Level Expression of Maize Phosphoenolpyruvate Carboxylase in Transgenic Rice Plants", Nature Biotechnology vol. 17 Jan. 1999, pp. 76-80.

Leiter H et al: "Purification, cDNA Cloning And Expression Of GDP-L-Fuc:Asn-Linked GlcNAc Alpha-1,3-Fucosyltransferase From Mung Beans" Journal Of Biological Chemistry, American Society Of Biological Chemists, Baltimore, Md, Us, Vo. 274, No. 31, Jul. 30, 1999, pp. 21830-21839.

Lerouge P et al: "N-Glycoprotein Biosynthesis In Plants: Recent Developments And Future Trends", Plant Molecular Biology, Nijhoff Publishers, Dordrecht, NL., vol. 38, 1998, pp. 31-48.

Lerouge P et al: "N-Glycosylation Of Recombinant Pharmaceutical Glycoproteins Produced In Transgenic Plants: Towards An Humanisation Of Plant N-Glycans" Current Pharmaceutical Biotechnology, Bentham Science Publishers, Boca Raton, FL, US, vol. 1, No. 2, 2000, pp. 347-354.

Li Bo et al: "Cloning, Expression And Characterization Of A cDNA (6a8) Encoding A Novel Human Alpha-Mannosidase" European Journal Of Biochemistry, Vo. 267, No. 24, Dec. 2000, pp. 7176-7182.

Maras M et al: "In Vitro Conversion Of The Carbohdryate Moiety Of Fungal Glycoproteins To Mammalian-Type Oligosaccharides", European Journal Of Biochemistry, Berline, De, vol. 249, 1997, pp. 701-707.

Miyake et al.: Purification of Human Erythropoietin:, The Journal of Biological Chemistra, vol. 252, No. 15 Issue of Aug. 10, pp. 5558-5564, 1977 Printed U.S.A.

Miyoshi E et al: "The Alpha 1-6-Fucosyltransferace Gene And Its Biological Significane" BBA—General Subjects, Elseviers Science Publishers, NL, vol. 1473, No. 1, Dec. 17, 1999.

Mokrzycki-Issartel Nathalie et al: "A Transient Tobacco Expression System Coupled To MALDI-ToF-MS Allows Validation Of The Impact Of Differential Targeting On Structure And Activity Of A Recombinant Therapeutic Glycoprotein Produced In Plants." Febs Letters, vol. 552, No. 2-3. Sep. 25, 2003, pp. 170-176.

Palacpac Nirianne Q et al: "Structures Of N-Linked Oligosaccharides Of Glycoproteins From Tobacco By2 Suspension Cultured Cells." Bioscience Biotechnology And Biochemistry, vol. 63, No. 1, Jan. 1999, pp. 35-39.

Rayon Catherine et al: "N-Glycosylation Of Phytohemagglutinin Expressed In Bean Cotyledons Or In Transgenic Tobacco Cells", Plant Physiology And Biochemistry (Paris), vol. 34, No. 2, 1996, pp. 273-281.

Rothman "Protein Sorting by Selective Retention in the Endoplasmic Reticulum and Golgi Stack" 1987, Cell. Aug. 14 50(4):521-2.

Schachter et al. "The 'yellow brick road' to Branched Complex N-glycans", 1991 Glycobiology 1:453-461.

Strasser R et al: "Molecular Cloning Of cDNA Encoding N-Acetylglucosaminyltransferace II From *Arabidopsis thaliana*" Glycoconjugate Journal, vol. 16, No. 12, Dec. 1999, pp. 787-791.

Tang B L et al: "The Transmembrane Domain Of N-Glucosaminyltransferase I Contains A Golgi Retention Signal", Journal Of Biological Chemistry, American Society Of Biological Chemists, Baltimore, MD, US, vol. 267, No. 14, 1992, pp. 10122-10126.

Taniguchi N. et al: A Glycomic Approach To The Identification And Characterization Of Glycoprotein Function In Cells Transfected With Glycosyltransferase Genes, Proteomics, vol. 1, No. 2, Feb. 2001, pp. 239-247.

Van Engelen F A et al: "Coordinate Expression Of Anitbody Subunit Genes Yields High Levels Of Functional Antibodies In Roots Of Transgenic Tobacco", Plant Molecular Biology, NL, Nijhoff Publishers, Dordrecht, vol. 26, No. 26, 1994, pp. 1701-1710-1710.

Vitale And Chrispeels 1984 J Cell Biol 99 133-140.

Voelker T A et al: "In-Vitro Mutated Phytohemagglutinin Genes Expressed In Tobacco Seeds: Role Of Glycans In Protein Targeting And Stability" Plant Cell, vol. 1, No. 1, 1989, pp. 95-104.

Wee EG. et al.: "Targeting Of Active Sialyltransferase To The Plant *Golgi aparatus*", Plant Cell, Oct. 1998, 1759-68.

Wright A et al: "Effect of Glyvcosylation On Antibody Function: Implications For Genetic Engineering", Trends In Biotechnonogy, Gb, Elsevier Publications, Cambridge, vol. 15, No. 1, Jan. 1, 1997, pp. 26-30.

Yin ZC et al: "Obtaining Transgenic Rice Plants and Their Progenies Using *Agrobacterium tumefaciens*" Translated Chinese Yi Chuan Xue Bao Dec. 1998;25(6): 517-24. PMID: 10465898.

Yizhang et al: Transformation Of Tobacco Using Human B-1,4-Galactosyltransferase Gene And Regeneration Of Transgenic Plants, 1995, ICBiotech, vol. 18, pp. 241-247.

Yoshida K et al: "Molecular Biology And Application Of Plant Peroxidase Genes.", Applied Microbiology And Biotechnology, vol. 60, No. 6, Feb. 2003, pp. 665-670.

Zhang et al.: "Agrobacterium-Mediated Transformation of Elite Indica and Japonica Rice Cultivars" Molecular Biotechnology 1997 Humana press, pp. 223-231.

Zhang et. al. "Quantative Analysis And Process Monitoring Of Site-Specific Glycoslyation Microheterogeneity In Recombinant Human Interferon-Y From Chinese Hamster Ovary Cell Culture By Hydrophyilic Interaction Chromatography", (1998) Journal of Chromatography B, 712, 73-82.

Zhu Guofen et al: "Beta-1,4 N-Acetylgalactosaminytransferase (Gm2/Gd2/Ga2 Synthase) Forms Homodimers In The Endoplasmic Reticulum: A Strategy To Test For Dimerization Of Golgi Membrane Proteins" Glycobiology, vol. 7, No. 7, 1997, pp. 987-996.

Shah et al., Sialylated endogenous glycoconjugates in plant cells. Nat Biotechnol. 2003 Dec.; 21(12):1470-1. Epub Nov. 9, 2003.

IB 03/001562 International Search Report Sep. 25, 2003.

IB 03/001562 International Preliminary Examination Report Mar. 18, 2003.

IB 03/001626 International Search Report Sep. 25, 2003.

IB 03/001626 International Preliminary Examinationa Report Jul. 22, 2004.

Asano et al., Growth retardation and early death of beta-1, 4-galactosyltranferase knockout mice with augmented proliferation and abnormal differentiation of epithelial cells. Embo J. Apr. 15, 1997; 16(8):1850-7.

Chrispeels et al., The production of recombinant glycoproteins with defined non-immunogenic glycans. In: Transgenic plants: a production system for industrial and pharmaceutical proteins. John Wiley Pub, UK. (1996)99-113.

Fischer et al., Molecular farming of pharmaceutical proteins. Transgenic Research. 2000;9:279-299.

Fuchs et al., Purification and characterization of microbially expressed neomycin phosphotransferase II (NPTII) protein and its equivalence to the plant expressed protein. Biotechnology (N Y). Dec. 1993;11(13):1537-42.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Herman et al., Three proteins involved in Caenorhabditis elegans vulval invagination are similar to components of a glycosylation pathway. Proc Natl Acad Sci U S A. Feb. 2, 1999;96(3):974-9.

Hein et al., Evaluation of immunoglobulins from plant cells. Biotechnol Prog. Sep-Oct. 1991;7(5):455-61.

Ioffe et al., Mice lacking N-acetylglucosaminyltransferase I activity die at mid-gestation, revealing an essential role for complex or hybrid N-linked carbohydrates, Proc Natl Acad Sci U S A. Jan. 18, 1994;91(2):728-32.

James et al., Production and characterization of biologically active human GM-CSF secreted by genetically modified plant cells. Protein Expr Purif. Jun. 2000;19(1):131-8.

Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002,;73-109.

Madson et al., Altered xyloglucans of arabidopsis thalianamutants bind normally to cellulose in vivo and in vitro. Poster from Plant Biology(Rockville) Jul. 27, 2001 Abstract #527.

Magnuson et al., Secretion of biologically active human interleukin-2 and interleukin-4 from genetically modified tobacco cells in suspension culture. Protein Expr Purif. Jun. 1998;13(1):45-52.

Magnuson et al., Enhanced recovery of a secreted mammalian protein from suspension culture of genetically modified tobacco cells. Protein Expr Purif. Mar. 1996;7(2):220-8.

Masri et al., Identification of the full-length coding sequence for human galactosyltransferase (beta-N-acerylglucosaminide: beta 1,4-galactosyltransferase). Biochem Biophys Res Commun. Dec. 15, 1988;157(2):657-63.

Seveno et al., Glycoprotein sialyation in plants? Nat Biotechnol. Nov. 22, 2004;22(11):1351-2.

Terayama et al., Cloning and functional expression of a novel glucuronyltranferase involved in the biosynthesis of the carbohydrate epitope HNK-1. Proc Natl Acad Sci U S A. Jun. 10, 1997;94(12):6093-8.

Van Ree et al., Beta(1,2)-xylose and aplha(1,3)-fucose residues have a strong contribution in lgE binding to plant glycoallergens. J Biol Chem,. Apr. 14, 2000;275(15):11451-8.

Warner et al., Metabolic engineering glycosylation: biotechnology's challenge to the glycobiologist in the next millenium; Carbohydrates in chemistry and biology, part II vol. 4. editors Earnst et al. (2000) Wiley-VCH. 1042-1064.

Wilson et al., Core alphal,3-fucose is a key part of the epitope recognized by antibodies reacting against plant N-linked Oligosaccharides and is present in a wide variety of plant extracts. Glycobiology. Jul. 1998;8(7):651-61.

Wilson et al., Cloning and expression of cDNAs encoding alpha1,3-fucosyltransferase homologues from Arabidopsis thaliana. Biochim Biophys Acta. Jul. 2, 2001;1527(1-2):88-96.

Yamaguchi et al., Genomic structure and promoter analysis of the human alpha1, 6-fucosyltransferase gene (FUT8). Glycobiology. Jun. 2000;10(6):637-43.

Yoshida et al., Expression of β1 4 galactosyltransferase in tobacco culture cell. Program for Congress of the Society for Bioscience and Bioengineering of Japan. Sep. 15, 1995;324:88.

Sakai et al., "Expression of Human β1,4-Galactosyltranferase in Tobacco BY2 Cells Modifies Glycosylation Patterns of Interacellular and Extracellular Glycoproteins," Translation of Abstract from the Ann. Meeting of Japan Society for Bioscience, Biotechnology, and Agrochemistry, Published Mar. 1998. (Additional translation of Sakai et al previously submitted).

Yosida et al., "Challenge for production of human-compatible glycoprotein therapeutics in yeast", Bioscience and Industry, vol. 54, pp. 420-422 (1996).

Sakai et al., Fatty Acid acylation of apoE by human monocyte/marophanges and helptocytes. Apr. 1998; 417. Abstract.

Sakai et al., Human glycosyltranferase expression and intracellular/intercellular glycoprotein sugar chain structure in cultured tobacco BY2 cells. Corrected title: Expression of human β 1,4-galactosyltransferase in tobacco BY2 cells modifies glycosylation patterns of intracellular and extracellular glycoproteins. IC Biotech. Osaka, Nara Institute. Mar. 1998, Abstract.

1) High Mannose-Type

2) Complex-Type

3) Hybrid-Type

C: M7A (9.3%)

F: M7B (15.9%)

G: M6B (19.5%)

J: M3X (6.6%)

K-1: M5 (1.4%)

K-2: GalGNM3 (11.8%)

L: GalGNM5 (35.5%)

METHOD FOR MANUFACTURING GLYCOPROTEINS HAVING HUMAN-TYPE GLYCOSYLATION

This application is a divisional patent application of U.S. patent application Ser. No. 09/857,651, filed Aug. 27, 2001, now U.S. Pat. No. 6,998,267, which claims priority to National Stage application of International Application No. PCT/JP99/06881, filed 08 Dec. 1999, now Publication No. WO 00/34490, published 15 Jun. 2000 in English; which claims priority to JP 10-350584, filed 09 Dec. 1998, all of which are herein incorporated by reference in their entirety.

TECHNICAL FIELD

The present invention relates to expression of exogenous glycoproteins by plants.

BACKGROUND ART

Many of the functional proteins in living organisms are glycoproteins. It has been elucidated that the diversity of the sugar chains in glycoproteins play several important roles physiologically (Lain, R. A., Glycobiology, 4, 759–767, 1994).

In recent years, it has also become clear that the action of sugar chains can be divided into two categories. In the first case, sugar chains have a direct function as ligands for binding cells, or as receptors for bacteria and viruses, in the clearance of glycoproteins from the blood, lysosome targeting of lysosome enzymes and the targeting by glycoproteins toward specific tissues and organs. For example, the contribution of glycoprotein sugar chains in the infection of target cells by the AIDS virus (HIV) has been established (Rahebi, L. et al., Glycoconj. J., 12, 7–16, 1995). The surface of HIV is covered-with envelope protein gp120. The binding of gp120 sugar chains to the CD4 of target cells is the beginning of infection by the HIV virus. In the second case, the sugar chain itself is not the functional molecule but indirectly contributes to the formation of the higher-order structure of proteins, solubility of proteins, protease resistance of proteins, inhibition of antigenicity, protein function modification, protein regeneration rate adjustment, and adjustment of the amount of proteins expressed in cell layers. For example, sugar chains are instrumental in the adjustment of the adhesion of nerve cell adhesion molecules which are distributed widely in the nervous system (Edelman, G. M., Ann. Rev. Biochem., 54, 135–169, 1985).

In eukaryotes, glycoprotein sugar chains are synthesized on lipids of the Endoplasmic reticulum as precursor sugar chains. The sugar chain portion is transferred to the protein, then some of the sugar residues on the protein are removed in the Endoplasmic reticulum, and then the glycoprotein is transported to Golgi bodies. In the Goldi bodies, after the excess sugar residues have been removed, further sugar residues (e.g. mannose) are added and the sugar chain is extended (Narimatsu, H., Microbiol. Immunol., 38, 489–504, 1994).

More specifically, for example, Glc3Man9GlcNAc2 on dolichol anchors is transferred to protein in the ER membrane (Moremen K. W., Trimble, R. B. and Herscovics A., *Glycobiology* Apr. 4, 1994 (2):113–25, Glycosidases of the asparagine-linked oligosaccharide processing pathway: and Sturm, A. 1995 N-Glycosylation of plant proteins. In: New Comprehensive Biochemistry. Glycoproteins, Vol. 29a., Montreuil, J., Schachter, H. and Vliegenthart, J. F. G. (eds). Elsevier Science Publishers B.V., The Netherland, pp. 521–541). ER-glucosidase I and II removes three glucose units (Sturm, A. 1995, supra; and Kaushal G. P. and Elbein A. D., 1989, Glycoprotein processing enzymes in plants. In Methods Enzymology 179, Complex Carbohydrates Part F. Ginsburg V. (ed), Academic Press, Inc. NY, pp. 452–475). The resulting high mannose structure (Man9GlcNAc2) is trimmed by ER-mannosidase (Moremen K. W. et al, supra,: and Kornfeld, R. and Kornfeld, S., Annu. Rev. Biochem. 54, 631–664, 1985; Assembly of asparagine-linked oligosaccharides). The number of mannose residues removed varies according to the differences in the accessibility to the processing enzymes. The isomers Man8-, Man7-, Man6- and Man5GlcNAc2 are produced during processing by ER-mannosidase and Mannosidase I (Kornfeld, R. and Kornfeld, S., supra). When four mannose residues are completely removed by Mannosidase I (Man I), the product is Man5GlcNAc2. N-acetylglucosaminyl transferase I (GlcNAc I) transfers N-acetylglucosamine (GlcNAc) from UDP-GlcNAc to Man5GlcNAc2, resulting in GlcNAcMan5GlcNAc2 (Schachter, H., Narasimhan, S., Gleeson, P., and Vella, G., Glycosyltransferases involved in elongation of N-glycosidically linked oligosaccharides of the complex or N-acetylgalactosamine type. In Methods Enzymol 98: Biomembranes Part L. Fleischer, S., and Fleischer, B. (ed), Academic Press, Inc. NY, pp. 98–134 pp. 98–134, 1983). Mannosidase II (Man II) removes two mannose residues from GlcNAcMan5GlcNAc2, yielding GlcNAcMan3GlcNAc2 (Kaushal, G. P. and Elbein, A. D., supra; and Kornfeld, R. and Kornfeld, S., supra). The oligosaccharide GlcNAcMan4GlcNAc2 is used as a substrate of N-acetylglucosaminyl transferase II (GlcNAc II (Moremen K. W. et al, supra,: Kaushal, G. P. and Elbein, A. D., supra: and Kornfeld, R. and Kornfeld, S., supra). FIG. 19 summarizes the above described structures of N-linked glycans and enzymes involved in sugar chain modification pathway in the Endoplasmic reticulum and Goldi bodies. In FIG. 19, ◇ denotes glucose, □ denotes GlcNAc, ○ denotes mannose, ● denotes galactose, and ■ denotes sialic acid, respectively.

The sugar addition in the Golgi bodies is called terminal sugar chain synthesis. The process differs widely among living organisms. The sugar chain synthesis depends on the type of eukaryote. The resulting sugar chain structure is species-specific, and reflects the evolution of sugar adding transferase and the Golgi bodies (Narimatsu, H., Cellular Biology, 15, 802–810, 1996).

Regarding aspargine-linked (N-linked) sugar chains; in animals, there are high mannose-type sugar chains, complex-type sugar chains and hybrid-type sugar chains. These structures are shown in FIG. 1. The complex-type sugar chains in plants have α1,3 fucose and β1,2 xylose which are sugar residues that are not found in animals (Johnson, X. D. and Chrispeels, M. J., Plant Physiol., 84, 1301–1308, 1897, Kimura, Y. et al., Biosci. Biotech. Biochem., 56, 215–222, 1992). In the case of N-linked sugar chains, sialic acid has been found in animal sugar chains but has not been found in plant sugar chains. Regarding galactose, which is generally found in animal sugar chains, although the presence thereof has been found in some plant sugar chains (Takahashi, N. and Hotta, T., Biochemistry. 25, 388–395, 1986), the examples thereof are few. The linkage-type thereof is a β1,3 linkage (FEBS Lett Sep. 29, 1997 415(2). 186–191, Identification of the human Lewis(a) carbohydrate motif in a secretory peroxidase from a plant cell suspension culture (*Vaccinium mytillus* L.)., Melo N S, Nimtz M, Contradt H S, Fevereiro P S, Costa J; Plant J. Dec. 12, 1997 (6), 1411–1417, N-glyeans harboring the Lewis a epitope are expressed at the surface of plant cells. Fitchette-Laine A C, Gomord V, Cabanes M, Michalski J C, Saint Macary M, Foucher B, Cavelier B, Hawes C, Lerouge P, Faye L). This linkage is different from those found in animals.

Glycoproteins derived from humans include human erythropoietin (EPO). In order to produce glycoproteins with sugar chain structures similar to humans, these glycoproteins are produced in animal host cells. However, EPO produced in animal cells has a sugar chain structure that is different from the natural human sugar chain structure. As a result, in vivo activity of EPO is reduced (Takeuchi, M. et al., Proc. Natl. Acad. Sci. USA, 86, 7819–7822, 1989). The sugar chain structure in other proteins derived from humans, such as hormones and interferon, have also been analyzed and manufactured with the same glycosylation limitations.

The methods used to introduce exogenous genes to plants include the *Agrobacterium* method (Weising, K. et al., Annu. Rev. Genet., 22, 421, 1988), the electroporation method (Toriyama, K. et al., Bio/Technology, 6, 1072, 1988), and the gold particle method (Gasser, C. G. and Fraley, R. T., Science, 244, 1293, 1989). Albumin (Sijmons, P. C. et al., Bio/Technology, 8, 217, 1990), enkephalin (Vandekerckhove, J. et al., Bio/Technology, 7, 929, 1989), and monoclonal antibodies (Benvenulo, E. et al., Plant Mol. Biol., 17, 865, 1991 and Hiatt, A. et al., Nature, 342, 76, 1989) have been manufactured in plants. Hepatitis B virus surface antigens (HBsAg) (Mason, H. S. et al., Proc. Natl. Acad. Sci. USA., 89, 11745, 1992) and secretion-type IgA (Hiatt., A. and Ma,: J. S. K., FEBS Lett., 307, 71, 1992) have also been manufactured in plant cells. However, when human-derived glycoproteins are expressed in plants, the sugar chains in the manufactured glycoproteins have different structures than the sugar chains in the glycoproteins produced in humans because the sugar adding mechanism in plants is different from the sugar adding mechanism in animals. As a result, glycoproteins do not have the original physiological activity and may be immunogenic in humans (Wilson, I. B. H. et al., Glycobiol., Vol. 8, No. 7, pp. 651–661, 1998).

DISCLOSURE OF THE INVENTION

The purpose of the present invention is to solve the problems associated with the prior art by providing plant-produced recombinant glycoproteins with mammalian, e.g., human-type sugar chains.

The present invention is a method of manufacturing a glycoprotein having a human-type sugar chain comprising a step in which a transformed plant cell is obtained by introducing to a plant cell the gene of an enzyme capable of conducting a transfer reaction of a galactose residue to a non-reducing terminal acetylglucosamine residue and the gene of a exogenous glycoprotein, and a step in which the obtained transformed plant cell is cultivated.

In the present invention, the glycoprotein with a human-type sugar chain can comprise a core sugar chain and an outer sugar chain, the core sugar chain consists essentially of a plurality of mannose and acetylglucosamine, and the outer sugar chain contains a terminal sugar chain portion with a non-reducing terminal galactose.

In the present invention, the outer sugar chain can have a straight chain configuration or a branched configuration.

In the present invention, the branched sugar chain portion can have a mono-, bi-, tri- or tetra configuration.

In the present invention, the glycoprotein can contain neither fucose nor xylose.

The present invention is also a plant cell having a sugar chain adding mechanism which can conduct a transfer reaction of a galactose residue to a non-reducing terminal acetylglucosamine residue, wherein the sugar chain adding mechanism acts on a sugar chain containing a core sugar chain and an outer sugar chain, wherein the core sugar chain consists essentially of a plurality of mannose and acetylglucosamine, and wherein the outer sugar chain contains a terminal sugar chain portion with a non-reducing terminal galactose.

In the present invention, a glycoprotein with a human-type sugar chain is obtained using this method.

BRIEF DESCRIPTION OF DRAWINGS

FIG 2(A) shows positions of the hGT-5Eco, hGT-6Spe, and hGT-2Sal primers used to amplify template DNA for the hGT gene. FIG. 2(B) is a schematic drawing of the preparation of the hGT gene cDNA, which is cloned in pBluescript II SK+ vector.

FIG. 4 (A) shows electrophoresis after the genome DNA (40 µg) has been digested by EcoRI and HindIII. The numbers at the left indicate the position of the DNA molecular weight marker.

FIG. 4(B) shows a schematic drawing of a 2.2 kb fragment containing a promoter, hGT and terminator, which is integrated into the transformed cell.

FIG. 5 is a photograph of the Western blotting of immunoreactive protein from transformed tobacco BY2 cells (WT) and wild type tobacco BY2 cells (WT). The protein was denatured, electrophoresed on 10% SDS-PAGE, and then transferred electrically to nitrocellulose film. The samples were as follows: lane 1=GT1 cell extract; lane 2=GT6 cell extract; lane 3=GT8 cell extract; lane 4=GT9 cell extract; lane 5=wild type cell extract: lane 6=GT1 microsome fragment: lane 7=GT6 microsome fragment; lane 8=GT8 microsome fragment; lane 9=GT9 microsome fragment; lane 10=wild type microsome fragment.

FIG. 10(A) shows the results of isoelectric focusing and FIG. 10(B) shows the results of Western blotting. The abbreviations are as follows: WT=wild-type: BY2-HRP 1, 5 and 7=the clone numbers for BY2 cells transformed with a HRP gene; and GT-6-HRP 4, 5 and 8=the clone numbers for GT6 cells transformed with a HRP gene.

FIG. 16(A) shows the results from silver staining, and FIG. 16(B) shows the results from lectin $RCA_{120}$ staining. The lectin-stained filter was cut into strips and then probed using lectin $RCA_{120}$ pre-incubated with buffer alone (I and II) or incubated in buffer with excess galactose (III). In (II), HRP was treated with β-galactosidase from *Diplococcus pneumoniae* before SDS-PAGE. Lane 1 is a collected fraction containing BY2-HRP and Lane 2 is a collected fraction containing GT6-HRP. The numbers to the left refer to the location and the size (KDa) of the standard protein.

BEST MODE FOR CARRYING OUT THE INVENTION

Figure 1:
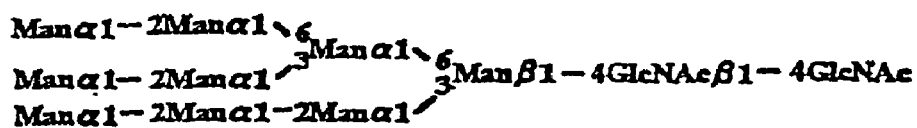
FIG. 1. A schematic drawing of typical N-linked sugar chain configurations.
Figure 1:
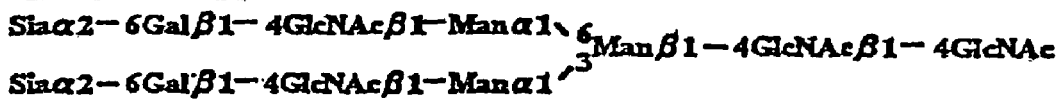
Figure 1:
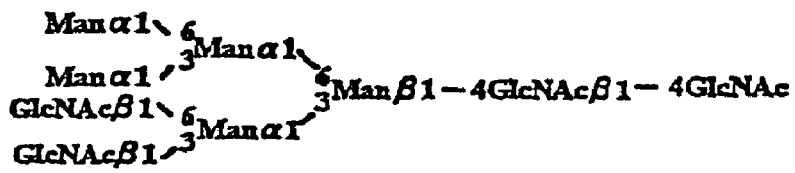

Hereinafter, the present invention will be described in further detail. In performing the present invention., unless otherwise indicated, any conventional technique can be used. These include methods for isolating and analyzing proteins as well as immunological methods. These methods can be conducted by using commercial kits, antibodies and markers.

The method of the present invention relates to a method of manufacturing glycoproteins with human-type sugar chains. In this specification, "human-type sugar chain" refers to a sugar chain with a galactose residue linked to a N-acetylglucosamine residue. The galactose residue in the human-type sugar chain can be the terminal sugar chain or a sialic acid residue can be linked to the outside of the galactose residue. Preferably, the glycoprotein of the present invention at least has no xylose or fucose linked to one or more of the following portions: the core sugar chain portion, the branched sugar chain portion, or the terminal sugar chain portion of the human-type sugar chain. More preferably, neither xylose or fucose should be linked to any portion of the human-type sugar chain, and ideally there should be no xylose or fucose contained in the human-type sugar chain at all.

The plant cells can be any plant cells desired. The plant cells can be cultured cells, cells in cultured tissue or cultured organs, or cells in a plant. Preferably, the plant cells should be cultured cells, or cells in cultured tissue or cultured organs. Most preferably, the plant cells should be cells in whole plants, or portions thereof, that produce glycoproteins with human-type sugar chains. The type of plant used in the manufacturing method of the present invention can be any type of plant that is used in gene transference. Examples of types of plants that can be used in the manufacturing method of the present invention include plants in the families of Solanaceae, Poaeae, Brassicaceae, Rosaceae, Leguminosae, Curcurbitaceae, Lamiaceae, Liliaceae, Chenopodlaceae and Umbelliferae.

Examples of plants in the Solanaceae family include plants in the *Nicotiana, Solanum, Datura, Lycopersicon* and *Petunia* genera. Specific examples include tobacco, eggplant, potato, tomato, chili pepper, and petunia.

Examples of plants in the Poaeae family include plants in the *Oryza, Hordenum, Secale, Saccharum, Echinochloa* and *Zea* genera. Specific examples include rice, barley, rye, *Echinochloa crus-galli*, sorghum, and *maize*.

Examples of plants in the Brassicaceae family include plants in the *Raphanus, Brassica, Arabidopsis, Wasabia*, and *Capsella* genera. Specific examples include Japanese white radish, rapeseed, *Arabidopsis thaliana*, Japanese horseradish, and *Capsella bursa-pastoris*.

Examples of plants in the Rosaceae family include plants in the *Orunus, Malus, Pynus, Fragaria*, and *Rosa* genera. Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alfalfa*, and *Medicago* genera. Specific examples include soybean, adzuki bean, kidney beans, peas, fava beans, peanuts, clover, and alfalfa.

Examples of plants in the Curcurbitaceae family include plants in the *Luffa, Curcurbita*, and *Cucumis* genera. Specific examples include gourd, pumpkin, cucumber, and melon.

Examples of plants in the Lamiaceae family include plants in the *Lavandula, Mentha*, and *Perilla* genera. Specific examples include lavender, peppermint, and beefsteak plant.

Examples of plants in the Liliaceae family include plants in the *Allium, Lillium*, and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia*, and *Apitum* genera. Specific examples include Japanese udo, carrot, honewort, and celery.

Preferably, the plants used in the manufacturing method of the present invention should be tobacco, tomato, potato, rice, *maize*, radish, soybean, peas, alfalfa or spinach. Ideally, the plants used in the manufacturing method of the present invention should be tobacco, tomato, potato, *maize* or soybean.

In this specification, "an enzyme capable of conducting a transfer reaction of a galactose residue to a non-reducing terminal acetylglucosamine residue" refers to an enzyme capable of conducting a transfer reaction of a galactose residue to a non-reducing terminal acetylglucosamine residue produced when a sugar chain is added after synthesis of the protein portion of the glycoprotein in the plant cell. Specific examples of these enzymes include galactosyltransferase, galactosidase, and β-galactosidase. These enzymes can be derived from any animal desired. Preferably, these enzymes should be derived from a mammal, and ideally these enzymes should be derived from a human.

In this specification, "the gene of an enzyme capable of conducting a transfer reaction of a galactose residue to a non-reducing terminal acetylglucosamine residue" can be a gene which can be isolated from an animal cell using a nucleotide sequence of an encoded enzyme well known in the art, or commercially available genes altered for expression in plants.

In this specification, "gene" usually refers to the structural gene portion. A control sequence such as a promoter, operator and terminator can be linked to the gene so as to properly express the gene in a plant.

In this specification, "exogenous glycoproteins" refers to glycoproteins whose expression in plants is the result of genetic engineering methodologies. Examples of these exogenous glycoproteins include enzymes, hormones,: cytokines, antibodies, vaccines, receptors and serum proteins. Examples of enzymes include horseradish peroxidase, kinase, glucocerebrosidase, α-galactosidase, tissue-type plasminogen activator (TPA), and HMG-COA reductase. Examples of hormones and cytokines include enkephalin, interferon alpha, GM-CSF, G-CSF, chorion stimulating hormone, interleukin-2, interferon-beta, interferon-gamma, erythropoietin, vascular endothelial growth factor, human choriogonadotropin (HCG), leuteinizing hormone (LH), thyroid stimulating hormone (TSH), prolactin, and ovary stimulating hormone. Examples of antibodies include IgG and scFv. Examples of vaccines include antigens such as Hepatitis B surface antigen, rotavirus antigen, *Escherichia coli* enterotoxin, malaria antigen, rabies virus G protein, and HIV virus glycoprotein (e.g., gp120). Examples of receptors and matrix proteins include EGF receptors, fibronectin, al-antitrypsin, and coagulation factor VIII. Examples of serum proteins include albumin complement proteins, plasminogen, corticosteroid-binding globulin, throxine-binding globulin, and protein C.

In this specification, "genes of exogeneous glycoproteins" refers to a gene, which can be isolated from a cell using a nucleotide sequence of an encoded protein well known in the art, or commercially available genes altered for expression in plants.

The gene of the enzymes capable of conducting a transfer reaction of a galactose residue to a non-reducing terminal acetylglucosamine residue and the genes of exogenous glycoproteins can be introduced to the plant cells using a method well known in the art. These genes can be introduced separately or simultaneously. Examples of methods for introducing genes to plant cells include the *Agrobacterium* method, the electroporation method and the particle bombardment method.

Using any method well known in the art, the plant cells with introduced genes can be tested to make sure the introduced genes are expressed. Examples of such methods include silver staining or augmentation, Western blotting, Northern hybridization, and enzyme activity detection. Cells that express the introduced genes are referred to as transformed cells.

Transformed cells, which express enzymes capable of conducting a transfer reaction of a galactose residue to a non-reducing terminal acetylglucosamine residue and exogenous glycoproteins, express exogenous glycoproteins with human-type sugar chains. In other words, the transformed cells have human-type sugar chain adding mechanisms. By cultivating these transformed cells, glycoproteins with human-type sugar chains can be mass produced. Human-type glycoproteins contain core sugar chains and outside sugar chains. The core sugar chains consist essentially of a plurality of mannose or acetylglucosamine. The outside sugar chains in these glycoproteins contain non-reducing terminal sugar chain portions. The outside sugar chains can have a straight chain configuration or a branched chain configuration. The branched sugar chain portion has a mono-, bi-, tri- or tetra configuration. The glycoproteins manufactured using these transformed cells ideally do not contain any fucose or xylose.

These transformed plant cells can remain in a cultured state or can be differentiated into specific tissues or organs. Alternatively, they can also be generated into plants. In this case, the transformed plant cells can be present in the entire plant or in specific portions of the plant, such as seed, fruit, nut, leaf, root, stem or flower of the plant.

Glycoproteins with human-type sugar chains can be manufactured by the transformed plant cells and then be isolated or extracted from the plant cells. The method for isolating the glycoproteins can be any method well known in the art. The glycoproteins of the present invention can be used in foodstuffs while remaining inside the transformed cells, or the glycoproteins of the present invention can be administered to animals including humans without antigenicity because of the added human-type sugar chains.

Hereinafter, the present invention will be described in detail by way of illustrative, but not restrictive, examples.

EXAMPLE 1

Cloning Human β1,4 Galactose Transferase Genes

β1,4 Galactosyltransferase (hGT) genes (EC2.4.1.38) have already been cloned. A primary configuration consisting of 400 amino acids has been discovered (Masri, K. A. et al., Biochem. Biophys. Res. Commun., 157, 657–663, 1988).

(1) Primer Preparation and Template DNA

The following primers were prepared with reference to the report by Masri et al.

```
                                       (Sequence ID: 1)
hGT-5Eco:   5'-AAAGAATTCGCGATGCCAGGCGCGCGTCCCT-3'

(Sequence I.D: 2)
hGT-2Sal:   3'-TCGATCGCAAAACCATGTGCAGCTGATG-5'

(Sequence I.D: 3)
hGT-7Spe:   3'-ACGGGACTCCTCAGGGGCGATGATCATAA-5'

(Sequence I.D: 4)
hGT6Spe:    5'-AAGACTAGTGGGCCCCATGCTGATTGA-3'
```

Human genome DNA, human placenta cDNA, and human kidney cDNA purchased from Clontech were used as the template DNA.

(2) Cloning the hGT Gene CDNA (i) Human genome DNA was used as the template and hGT-5Eco and hGT-7Spe were used as the primers; (ii) Human placenta CDNA was used as the template and hGT-2Sal and hGT6Spe were used as the primers. The two were combined and a PCR reaction was performed under the following conditions. Then, 0.4 kb and 0.8 kb fragments containing hGT encoded areas were obtained.

(PCR reaction mixture) 1 μl template DNA, 5 μml 10×PCR buffer solution, 4 μl dNTPs (200 mM), the primers (10 pmol), and 0.5 μl (Takara Shuzo Co., Ltd.) Tag polymerase (or 0.2 μl Tub polymerase), water was added to make 50 μl.

(PCR Reaction Conditions) First Stage: 1 cycle, denaturation (94° C.) 5 minutes, annealing (55° C.) 1 minute, extension (72° C.) 2 minutes. Second Stage: 30 cycles, denaturation (94° C.) 1 minute, annealing (55° C.) 1 minute, extension (72° C.) 2 minutes. Third Stage: 1 cycle, denaturation (94° C.) 1 minute, annealing (55° C.) 2 minutes, extension (72° C.) 5 minutes.

Figure 2:
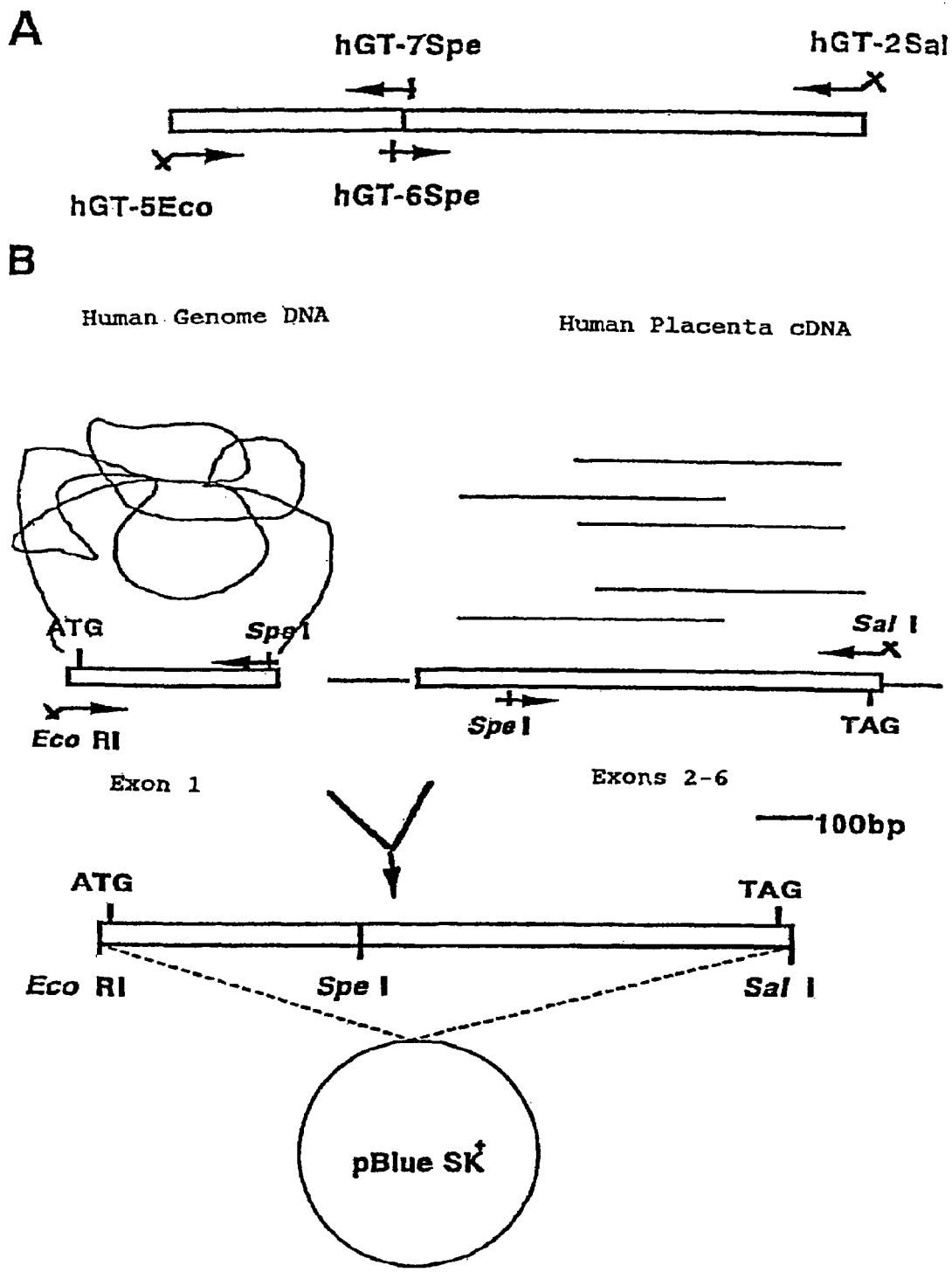
FIG. 2. Schematic drawings of the cloning method for hGT.

The two fragments were combined to form hGT gene cDNA and cloned in pBluescript II SK+ (SK). The pBluescript II SK+ (SK) was purchased from Stratagene Co., Ltd. FIG. 2 shows the structure of a plasmid containing hGT gene cDNA. This shows Sequence No. 5 In the hGT gene nucleotide sequence and Sequence No. 6 in the estimated amino acid sequence. This nucleotide sequence differed from the hGT sequence published by Masri et al. (see above) in the following ways:: a) The nucleotides are different in that the A in Position No. 528 is G, the C in Position No. 562 is T, and the A in Position No. 1047 is G, however the encoded amino acid sequence is not changed; b) Nine nucleotides at positions from Position No. 622 to Position No. 630 are missing; c) The G in Position No. 405 is A and the T in Position No. 408 is A.

These nucleotide changes were made during primer preparation such that the 0.4 kb fragment and 0.8 kb fragment are connected. There are two start codons (ATG) in hGT gene CDNA. In this experiment, however, the gene is designed such that translation begins from the second initial codon (Position No. 37).

EXAMPLE 2

Figure 3:
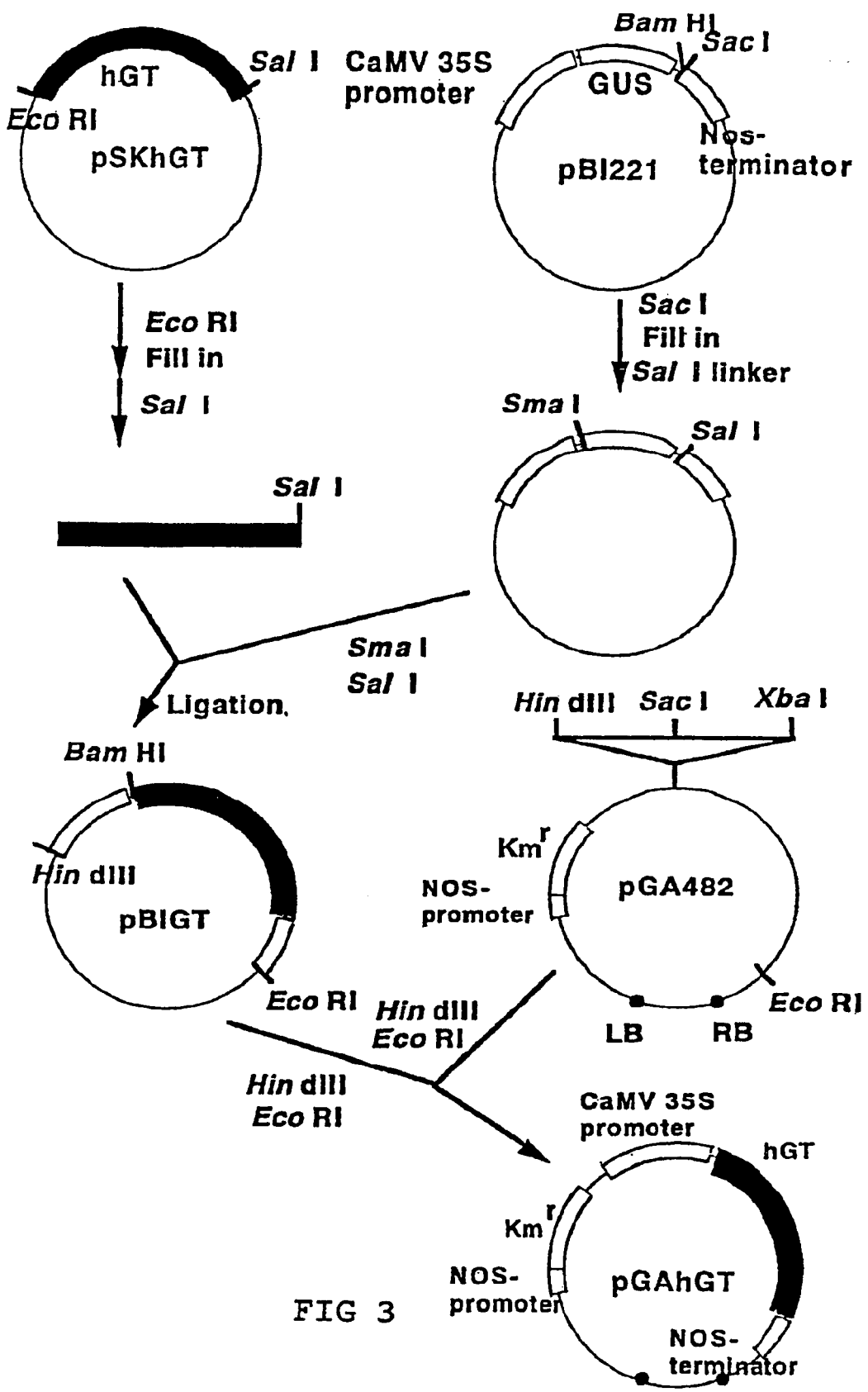
FIG. 3. Schematic drawings of the method used to construct vector pGAhGT for hGT expression.

Introduction of the hGT Gene to a Cultivated Tobacco Cell (1) It has been reported that hGT is expressed in an active form in *Escherichia coli* (Aoki, D. et al., EMBO J., 9, 3171, 1990 and Nakazawa, K. et al., J. Biochem., 113, 747, 1993). In order for a cultivated tobacco cell to express hGT, the expression vector pGAhGT had to be structured as shown in FIG. 3. A cauliflower mosaic virus 35S promoter (CaMV 35S promoter), which drives gene expression constitutively in plant cells, was used as the promoter. A kanamycin-resistance gene was used as the selection marker. The pGAhGT was introduced to the cultivated tobacco cell by means of *Agrobacterium* method.

The *Agrobacterium* method was performed using the triparental mating method of Bevan et al. (Bevan, M., Nucleic Acid Res., 12, 8711, 1984). *Escherichia coli* DH5α (suE44, DlacU169, (φ801acZDM15), hsdR17) (Bethesda Research Laboratories Inc.: Focus 8 (2), 9, 1986) with pGA-type plasmids (An. G., Methods Enzymol. 153, 292, 1987) and *Escherichia coli* HB101 with helper plasmid pRK2013 (Bevan, M, Nucleic Acid Res., 12, 8711, 1984) were left standing overnight and 37° C. in a 2×YT medium containing 12.5 mg/l tetracycline and 50 mg/l kanamycin, and *Agrobacterium tumefaciens* EHA101 was left standing over two nights at 28° C. in a 2×YT medium containing 50 mg/l kanamycin and 25 mg/l chloramphenicol. Then, 1.5 ml of each cultured medium was removed and placed into an Eppendorf tube. After the cells of each strain were collected, the cells were rinsed three times in an LB medium. The cells obtained in this manner were then suspended in 100 μl of a 2×YT medium, mixed with three types of bacteria, applied to a 2 ×YT agar medium, and cultivated at 28° C. whereby the pGA-type plasmids, then underwent conjugal transfer from the *E. coli* to the *Agrobacterium*. Two days later some of the colony appearing on the 2×YT agar plate was removed using a platinum loop, and applied to an LB agar plate containing 50 mg/l kanamycin, 12.5 mg/l tetracycline, and 25 mg/l chloramphenicol. After cultivating the contents for two days at 28° C., a single colony was selected.

Transformation of the cultivated tobacco cells was performed using the method described in An, G., Plant Mol. Bio. Manual, A3, 1. First, 100 μl of *Agrobacterzium* EHA101 with pGA-type plasmids cultivated for 36 hours at 28° C. in an LB medium containing 12.5 mg/l tetracycline and 4 ml of a suspension of cultivated tobacco cells *Nicotiana tabacum L.* cv. bright yellow 2 (Strain No. BY-2 obtained using Catalog No. RPC1 from the Plant Cell Development Group of the Gene Bank at the Life Science Tsukuba Research Center), in their fourth day of cultivation, were mixed together thoroughly in a dish and allowed to stand in a dark place at 25° C. Two days later, some of the solution was removed from the dish and the supernatant was separated out using a centrifuge (1000 rpm, 5 minutes). The cell pellet was introduced to a new medium and centrifuged again. The cells were innoculated onto a modified LS agar plate with 150–200 mg/l kanamycin and 250 mg/l carbenicillin. This was allowed to stand in darkness at 25° C. After two to three weeks, the cells grown to the callus stage were transferred to a new plate and clones were selected. After two to three weeks, the clones were transferred to a 30 ml modified LS medium with kanamycin and carbenicillin. This selection process was repeated over about one month. Six resistant strains were randomly selected from the resistant strains obtained in this manner (GT 1, 4, 5, 6, 8 and 9).

(2) Verification of the Introduced hGT Genes

In the resistant strains, a 2.2 kb fragment containing a CaMV35S promoter and an hGT gene cDNA-NOS terminator in the T-DNA was confirmed in the genomic DNA of the cultivated tobacco cells using a Southern blot analysis. The Southern method was performed after the genomic DNA had been prepared from the resistant strains mentioned above and digested by EcoRI and HindIII.

The preparation of the chromosomal DNA from the cultured tobacco cells was performed using the Watanabe method (Watanabe, K., Cloning and Sequence, Plant Biotechnology Experiment Manual, Nouson Bunka Co., Ltd.). First, 10 ml of the cultivated tobacco cells were frozen using liquid nitrogen, and then ground to powder using a mortar and pestle. About five grams of the powder was placed in a centrifuge tube (40 ml) rapidly such that the frozen powder did not melt and mixed with 5 ml of a 2×CTAB (cetyltrimethyl ammonium bromide) solution pre-heated to 60° C. This was well mixed, slowly for 10 minutes, and then allowed to stand at 60° C. Then, 5 ml of a chloroform:isoamylalcohol (24:1) solution was added, and the mixture was stirred into and emulsion. The mixture was then centrifuged (2,800 rpm, 15 minutes, room temperature). The surface layer was then transferred to a new 40 ml centrifuge tube and the extraction process was repeated using the chloroform:isoamylalcohol (24:1) solution. After the surface layer had been mixed with $\frac{1}{10}$ volume of 10% CTAB, it was centrifuged (2,800 rpm, 15 minutes, room temperature). The surface layer was transferred to a new centrifuge tube and then mixed with an equal volume of cold isopropanol. The thus obtained solvent mixture was then centrifuged (4,500 rpm, 20 minutes, room temperature). After the supernatant had been removed using an aspirator, it was added to 5 ml of a TE buffer solution containing 1 M sodium chloride. This was completely dissolved at 55–60° C. This was mixed thoroughly with 5 ml of frozen isopropanol and the DNA was observed. It was placed on the tip of a chip, transferred to an Eppendorf tube (containing 80% frozen ethanol), and then rinsed. The DNA was then rinsed in 70% ethanol and dried. The dried pellet was dissolved in the appropriate amount of TE buffer solution. Then, 5 ml of RNAase A (10 mg/ml) was added, and reacted for one hour at 37° C.; Composition of the 2×CTAB Solution: 2% CTAB, 0.1 M Tris-HCl (pH8.0), 1.4 M sodium chloride, 1% polyvinylpyrrolidone (PVP); composition of the 10% CTAB solution: 10% CTAB, 0.7 M sodium chloride.

The Southern blot method was performed in the following manner:

(i) DNA Electrophoresis and Alkali Denaturation: After 40 μg of the chromosomal DNA had been completely digested by the restriction enzyme, the standard method was used, and 1.5% agarose gel electrophoresis was performed (50 V). It was then stained with ethidium bromide and photographed. The gel was then shaken for 20 minutes in 400 ml of 0.25 M HCl, and the liquid removed, and the gel permeated with 400 ml of a denaturing solution (1.5 M NaCl, 0.5 M NaOH by shaking slowly for 45 minutes. Next, the liquid was removed, 400 ml of neutral solution (1.5 M NaCl, 0.5 M Tris-HCl pH 7.4) was added, and the solution was shaken slowly for 15 minutes. Then, 400 ml of the neutral solution was again added, and the solution was shaken slowly again for 15 minutes. (ii) Transfer: After electrophoresis, the DNA was transferred to a nylon membrane (Hybond-N Amersham) using 20×SSC. The transfer took more than 12 hours. After the blotted membrane was allowed to dry at room temperature for an hour, UV fixing was performed for five minutes. 20×SSC Composition: 3 M NaCl, 0.3 M sodium citrate. (iii) DNA Probe Preparation: The DNA probe preparation was performed using a Random Prime Labeling Kit (Takara Shuzo Co., Ltd.). Next, the reaction solution was prepared in an Eppendorf tube. After the tube was heated for three minutes to 95° C., it was rapidly cooled in ice. Then, 25 ng of the template DNA and 2 μl of the Random Primer were added to make 5 μl. Then, 2.5 μl 10×buffer solution, 2.5 μml dNTPs, and 5 μl [α-$^{32}$p] dCTP (1.85 MBq, 50 mCi) were added, and H$_2$O was added to bring the volume of reaction mixture to 24 μl. Then, 1 μl of a Klenow fragment was added and the solution was allowed to stand for 10 minutes at 37° C. It was then passed through a NAP10 column (Pharmacia Co., Ltd.) to prepare the purified DNA. After being heated for three minutes at 95° C., it was rapidly cooled in ice, and used as a hybridization probe. (iv) Hybridization: 0.5% (w/v) SDS was added to the following Pre-hybridization Solution, the membrane in (ii) was immersed in the solution, and pre-hybridization was performed for more than two hours at 42° C. Afterwards, the DNA probe prepared in (iii) was added, and hybridization was performed for more than 12 hours at 42° C. Composition of the Pre-hybridization Solution: 5×SSC, 50 mM sodium phosphate, 50% (w/v) formamide, 5× Denhardt's solution (prepared by diluting 100× Denhardt's solution), 0.1% (w/v) SDS. Composition of the 100× Denhardt's Solution: 2% (w/v) BSA, 2% (w/v) Ficol 400, 2% (w/v) polyvinylpyrrolidone (PVP). (v) Autoradiography: After rinsing in the manner described below, autoradiography was performed using the standard method. It was performed twice for 15 minutes at 65° C. in 2×SSC and 0.1% SDS, and once for 15 minutes at 65° C. in 0.1×SSC and 0.1% SDS.

Figure 4:
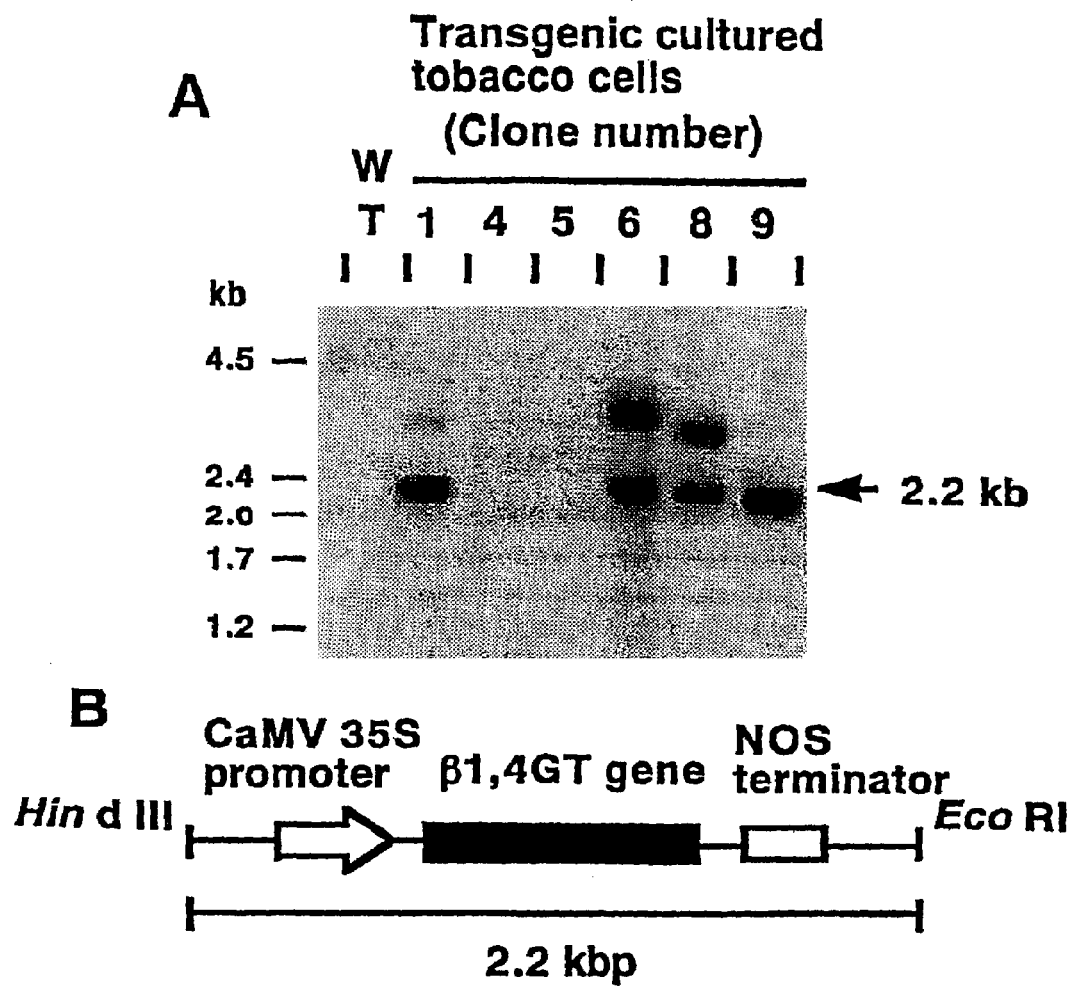
FIG. 4. A photograph showing a Southern blot analysis of a genome of cultivated transformed tobacco cells.

The results of the Southern blot analysis of the genome DNA prepared from the resistant strains are shown in FIG. 4. As shown in FIG. 4, the presence of the hGT gene was verified in four strains (GT1, 6, 8 and 9).

EXAMPLE 3

Analysis of the Galactosyltransferase Transformant

The cells of the transformants (GT-1, 6, 8 and 9) and wild-type BY-2 in the fifth through seventh day's culture both were harvested, and then suspended in extraction buffer solution (25 mM Tris-HCl, pH 7.4; 0.25 M sucrose, 1 mM MgCl$_2$, 50 mM KCl). The cells were ruptured using ultrasound processing (200 W; Kaijo Denki Co., Ltd. Japan) or homogenized. The cell extract solution and the microsome fractions were then prepared according to the method of Schwientek, T. et al. (Schwientek, T. and Ernst, J. F., Gene 145, 299–303, 1994). The expression of the hGT proteins was detected using Western blotting and anti-human galactosyltransferase (GT) monoclonal antibodies (MAb 8628: 1:5000) (Uejima, T. et al., Cancer Res., 52, 6158–6163, 1992; Uemura, M. et al., Cancer Res., 52, 6153–6157, 1992) (provided by Professor Narimatsu Hisashi of Soka University) Next, the blots were incubated with horseradish peroxidase-conjugated goat anti-mouse IgG (5% skim milk 1:1000; EY Laboratories, Inc., Calif.), and a colorimetric reaction using horseradish peroxidase was performed using the POD Immunoblotting Kit (Wako Chemicals, Osaka).

An immunoblot analysis of the complex glycans unique to plants was performed using polyclonal antiserum against β-fructosidase in the cell walls of carrots and horseradish peroxidase-conjugated goat anti-rabbit IgG antibodies (5% skim milk 1:1000; Sigma) (Lauriere, M. et al., Plant Physiol. 90, 1182–1188, 1989).

The β1,4-galactosyltransferase activity was assayed as a substrate using UDP-galactose and a pyridylamino (PA–)

labeled GlcNAc$_2$Man$_3$GlcNAc$_2$ (GlcNAC$_2$Man$_3$GlcNAc$_2$-PA) (Morita, N. et al., J. Biochem. 103, 332–335, 1988). The enzyme reaction solution contained 1–120 μg protein, 25 mM sodium cacodylate (pH 7.4), 10 mM MnCl$_2$, 200 mM UDP-galactose, and 100 nM GlcNAc$_2$Man$_3$GlcNAc$_2$-PA. An HPLC analysis was performed on the reaction product using PALPAK Type R and PALPAK Type N columns (Takara Shuzo Co., Ltd.) and the method recommended by the manufacturer. The GlcNAc$_2$Man$_3$GlcNAc$_2$-PA used as the standard marker was used along with Gal$_2$GlcNAc$_2$Man$_3$GlcNac$_2$-PA and two isomers of GalGlcNAc$_2$Man$_3$GlcNAc$_2$-PA purchased from Takara Shuzo Co. Ltd. and Honen Co., Ltd.

Figure 5:
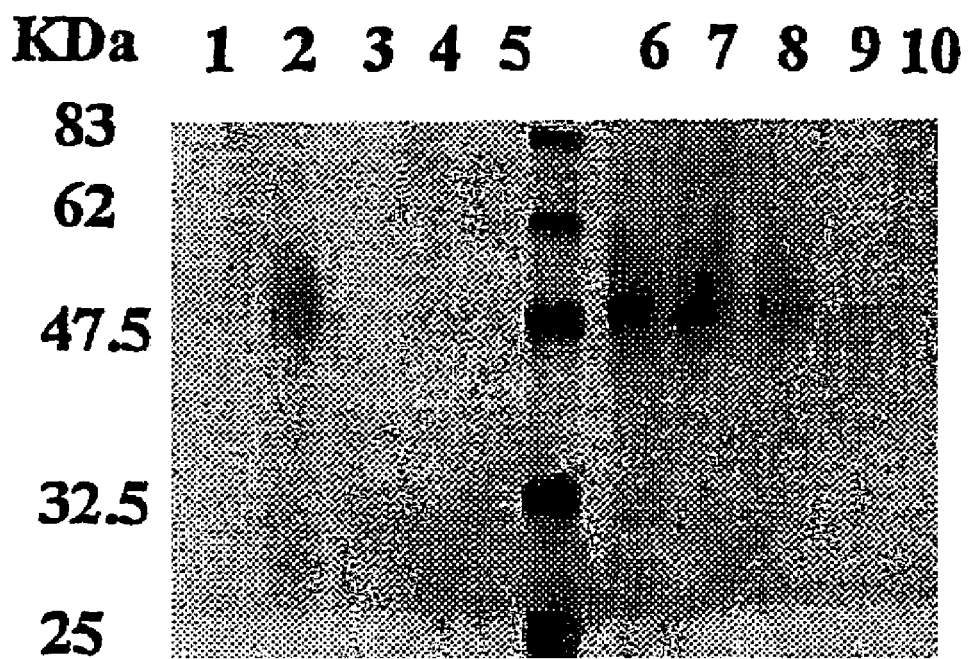
FIG. 5.

The immmunoblottings for the proteins derived from the transformant and the wild-type cells are shown in FIG. 5. As shown in FIG. 5, positive signals of a molecular weight of 50 kDa were observed. This is greater than the molecular weight estimated from the amino acid sequence (40 kDa) and is roughly equivalent to the bovine galactosyltransferase purified from ascites and expressed in yeast (Uemura, M. et al., Cancer Res., 52, 6153–6157, 1992; Schwientek, T. et al., J. Biol. Chem., 271 (7), 3398–3405, 1996). In the microsome fraction, immunoreactive bands (FIG. 5, Lanes 1,4) stronger than those of the cell lysate (FIG. 5, Lanes 6–8) were observed. This means that hGT is localized preferentially in the cell. No immunoreactive bands were detected in the wild-type cells.

Figure 6:
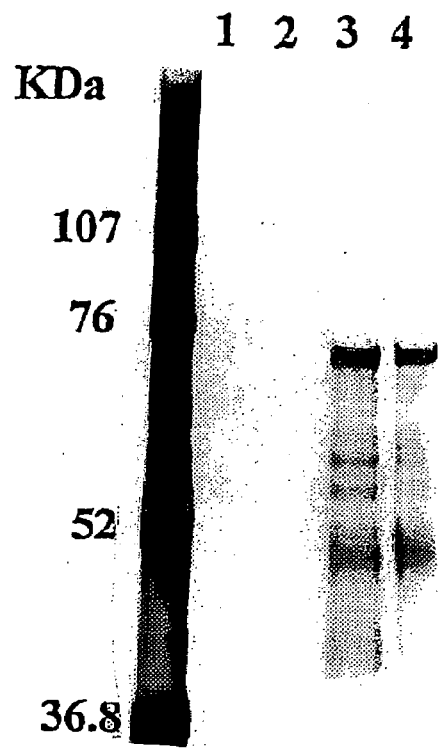
FIG. 6. An electrophoresis photograph showing the detection of galactosylated glycoprotein using *Ricinus communis* ($RCA_{120}$) affinity chromatography. The electrophoresed gel was visualized by silver staining. Lanes 1 and 2 show the protein from wild type BY2 cells, while Lanes 3 and 4 show the protein from transformed GT6 cells. The molecular weight is in KDa units.
Figure 7:
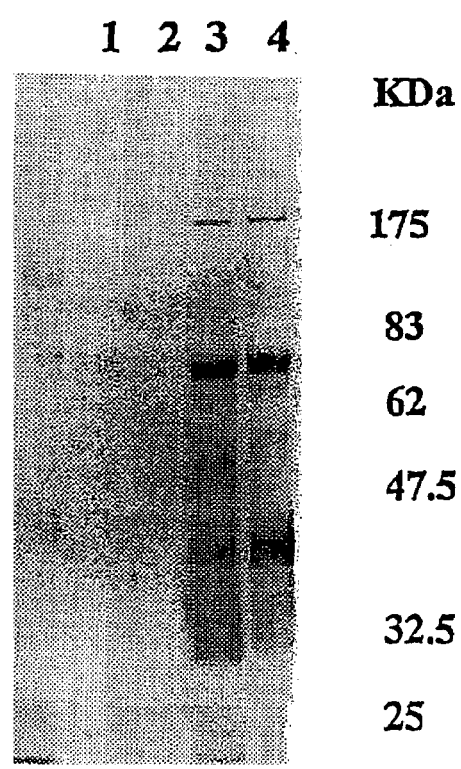
FIG. 7. A photograph of Western blotting a showing the detection of galactosylated glycoprotein using *Ricinus communis* ($RCA_{120}$) affinity chromatography. After the electrophoresed gel had been blotted on a nitrocellulose membrane, this membrane was visualized by lectin ($RCA_{120}$) staining. Lanes 1 and 2 show the protein from a wild type BY2 cell, while Lanes 3 and 4 show the protein from transformed GT6 cells. The molecular weight is in KDa.

The proteins in the microsome fractions of transformant GT6 and wild-type BY-2 were bound in an RCA$_{120}$ agarose column (Wako Chemicals, Osaka), and then rinsed with 15 volumes of 10 mM ammonium acetate pH 6.0. Next, the bound proteins were eluted using 0.2 M lactose. After separation using SDS-PAGE, the proteins were stained using silver staining (Wako Silver Staining Kit) (FIG. 6) or lectin (FIG. 7). In the lectin staining, the membrane blots were rinsed in a TTBS buffer solution (10 mM Tris-HCl,pH 7.4: 0.15 M NaCl: 0.05% Tween 20) and incubated with horseradish peroxidase labeled RCA$_{120}$ (Honen Co., Ltd.). Galactosylated glycan was then observed using a Immunoblotting Kit (Wako Chemicals, Osaka) (FIG. 7). As shown in FIG. 7, an RCA$_{120}$ binding was not observed in the wild-type BY2 cells, and the GT6 had a glycoprotein with galactose on the non-reducing terminus of the glycan portion.

Figure 8:
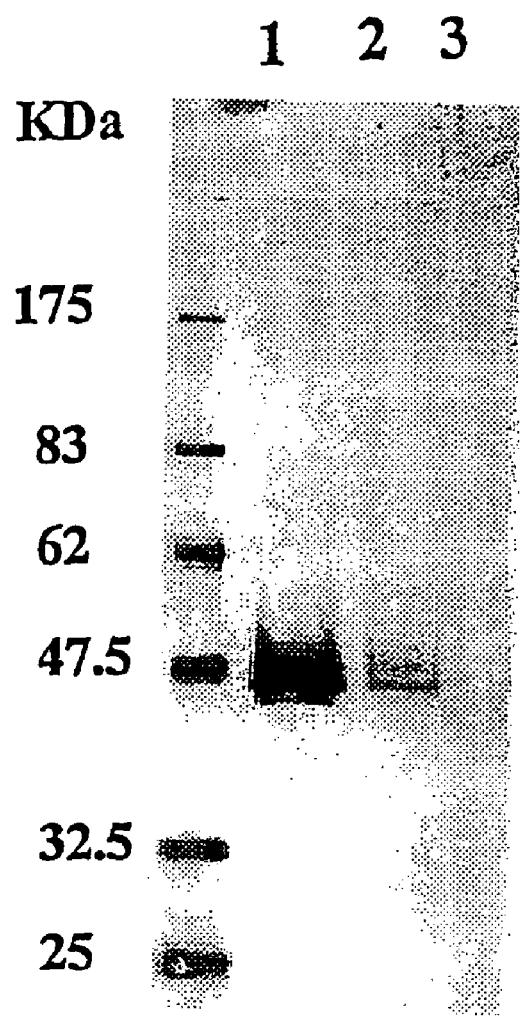
FIG. 8. A photograph of a blotting in which the galactosylated glycoprotein from *Ricinus communis* ($RCA_{120}$) affinity chromatography was probed with an antiserum specific to xylose in complex-type plant glycans. Lanes 1 and 2 show the total protein extracts from BY2 and GT6, respectively, and Lane 3 shows the glycoprotein from GT6 after $RCA_{120}$ affinity chromatography. The molecular weight is in KDa units.

The protein extract from the wild-type BY2 cells and the GT6 cells as well as the GT6 proteins eluted from the RCA$_{120}$ affinity chromatography were probed using polyclonal antibodies unique to complex glycan (FIG. 8). The antiserum binds predominantly to the β1,2-xylose residue on the plant glycoprotein (Lauriere, M. et al., Plant Physiol. 90, 1182–1188, 1989). As shown in FIG. 8, the wild-type BY2 cells (Lane 1) contain glycoproteins that reacted with the polyclonal antiserum. GT6 contains very few glycoproteins that reacted with the polyclonal antiserum (Lane 2). The GT6 glycoproteins eluted from RCA$_{120}$ affinity chromatography did not bind to the polyclonal antiserum, indicating that the galactosylated glycan does not contain β1,2-xylose residue (Lane 3).

EXAMPLE 4

Figure 9:
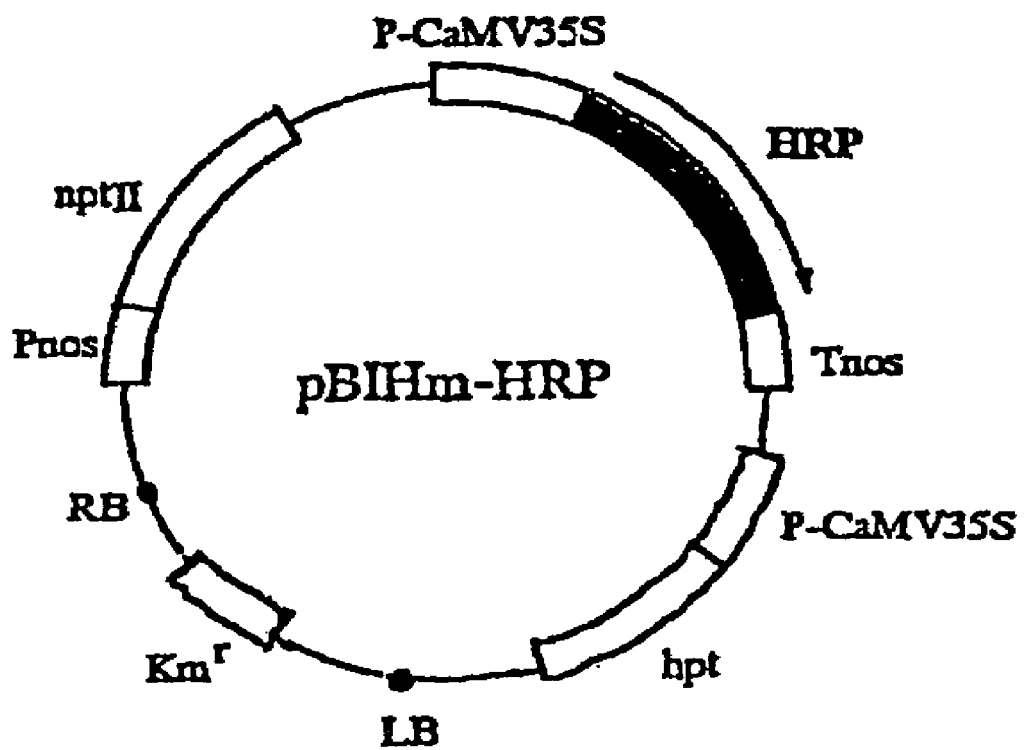
FIG. 9. A schematic drawing of a plasmid pBIHm-HRP which is a binary vector with a kanamycin-resistant gene and a hygromycin-resistant gene, and has a HRP cDNA.

Introduction of the Horseradish Peroxidase (HRP) Gene to the hGT-Introduced Cultivated Tobacco Cells Horseradish peroxidase gene was introduced to the resultant GT6 cell line. Among the different types of plant peroxidase horseradish peroxidase, especially HRP isozyme C, HRP (EC1.11.1.7) has been the subject of extensive research. HRP can be used in various enzyme reactions because of its superior stability and a broad spectrum of substance specificity. For example, it has been used in enzyme immunology for binding with a secondary antibody in Western blotting. A number of horseradish peroxidase isozyme genes have now been cloned (Fujiyama, K. et al., Eur. J. Biochem., 173, 681–687, 1988 and Fujiyama, K. et al., Gene, 89, 163–169, 1990). ClaPeroxidase (ClaPRX) which is encoded by prxCla is first translated as a protein consisting of 353 amino acids containing an extra peptide consisting of 30 amino acids at the N terminus and 15 amino acids at the C terminus. Then, this is processed to form a mature enzyme with 308 amino acids (Fujiyama, K. et al., Eur. J. Biochem., 173, 681–687, 1988). The molecular weight of ClaPiX ranges between 42,200 and 44,000. Of this molecular weight, sugar chains account for 22–27%, and there are eight N-linked sugar chains. (Welinder, K. G., Eur. J. Biochem., 96, 483–502, 1979). The introduction of the ClaPRX gene was performed using the binary vector pBIHm-HRP for HRP expression shown in FIG. 9.

The pBIHm-HRP was prepared in the following manner. First, a 1.9 kbp HindIII-SacI fragment was prepared from a vector 35S-prxCla for plant expression, which caries an HRP cDNA (Kawaoka, A. et al., J. Ferment. Bioeng. 78, 49–53, 1994).

The HindIII-SacI fragment contains a full length 1.1 kbp prxcla CDNA following a 0.8 kbp CaMV35S promoter. The 1.9 kbp HindIII-SacI fragment was inserted in the HindIII-SacI site of the binary vector pBI101HmB (Akama, K. et al., Plant Cell Rep., 12, 7–11, 1992). The BamHI site at 3' of the hygromycin resistant gene (HPT gene) had been destroyed.

Because the GT6 strain is kanamycin resistant, the hygromycin-resistant hpt gene was used as the selection marker (Griz, L. and Davies J., Gene, 25, 179–188, 1983). The transformation of the GT6 strain by HRP gene was performed using the method described in Rempel, D. H. and Nelson, L. M. (Rempel, D. H. and Nelson, L. M., Transgenic Res. 4: 199–207, 1995). In order to obtain HRP transformant as a control, an HRP gene was introduced to a wild-type BY2 cell to obtain a BY2-HRP strain. The double-transformant GT6-HRP with hGT and HRP was obtained in which an ordinary transformation process takes place.

EXAMPLE 5

Verification of the Expression of HRP in the Cultivated Double-Transformant Tobacco Cells Double transformant GT6-HRP, control BY2-HRP and wild-type (WT) cell line were examined for the expression of HRP activity using the following method. As seen in Table 1, the HRP gene-introduced transformant had peroxidase: activity about five times higher than the wild-type cell line.

TABLE 1

| Clone Number | Specific activity [U/mg protein] |
|---|---|
| WT-HRP-1 | 10.3 |
| WT-HRP-5 | 11.3 |
| WT-HRP-7 | 12.6 |
| GT-HRP-4 | 11.1 |
| GT-HRP-5 | 9.35 |
| GT-HRP-8 | 9.47 |
| Wild Type | 2.49 |

Clone BY2-HRP obtained by introducing the HRP gene to the wild type expressed the same degree of peroxidase activity as the GT6-HRP double transformant with hGT and HRP.

(Peroxidase Activity Measurement)

The cultivated tobacco cells were placed into an Eppendorf tube containing Solution D and were ruptured using a homogenizer (Homogenizer S-203, Ikeda Rika Co., Ltd.). The supernatant was collected after centrifugation (12,000 rpm, 20 minutes, 4° C.) and then used as the crude enzyme solution. Next, 1 ml of Solution A, 1 ml of Solution B and 2 ml of Solution C were mixed together, and the mixture was incubated for five minutes at 25° C. The crude enzyme solution appropriately diluted with Solution D was added to the mixture, and allowed to react for three minutes at 25° C. The reaction was stopped by the addition of 0.5 ml of 1 N HCl, and the absorbance at 480 nm was measured. As a control, a solution with 1 N HCl added before the introduction of the enzyme was used.

Solution A: 1 mM o-aminophenol
Solution B: 4 MM $H_2O_2$
Solution C: 200 mM sodium phosphate buffer (pH 7.0)
Solution D: 10 mM sodium phosphate buffer (pH 6.0)

Next, in order to determine whether or not the rise in peroxidase activity was due to the expression of HRP, activity staining was performed after separation by gel isoelectric focusing. The isoelectric focusing was performed using a BIO-RAD Model 111 Mini-IEF Cell. The hydrophobic surface of the PAGE gel support film was attached to a glass plate, and then placed on a casting tray. The prepared gel solution was poured between the support film and the casting tray and then photopolymerized for 45 minutes under a fluorescent lamp. The sample was applied to the gel, and the gel was positioned so as to come into contact with both graphite electrodes wetted with distilled water in the electrophoretic bath. Electrophoresis was then performed for 15 minutes at 100 V, 15 minutes at 200 V and 60 minutes at 450 V. Composition of the Gel Solution (per 1 Gel Sheet):distilled water 2.75 ml, acrylamide (25% T, 3% C) 1.0 ml, 25% glycerol 1.0 ml, Bio-lite (40%, pH 3–10) 0.25 ml, 10% ammonium persulfate 7.5 µl, 0.1% sodium riboflavin 5'-phosphate 25 µl, TEMED 1.5 µl.

Figure 10:
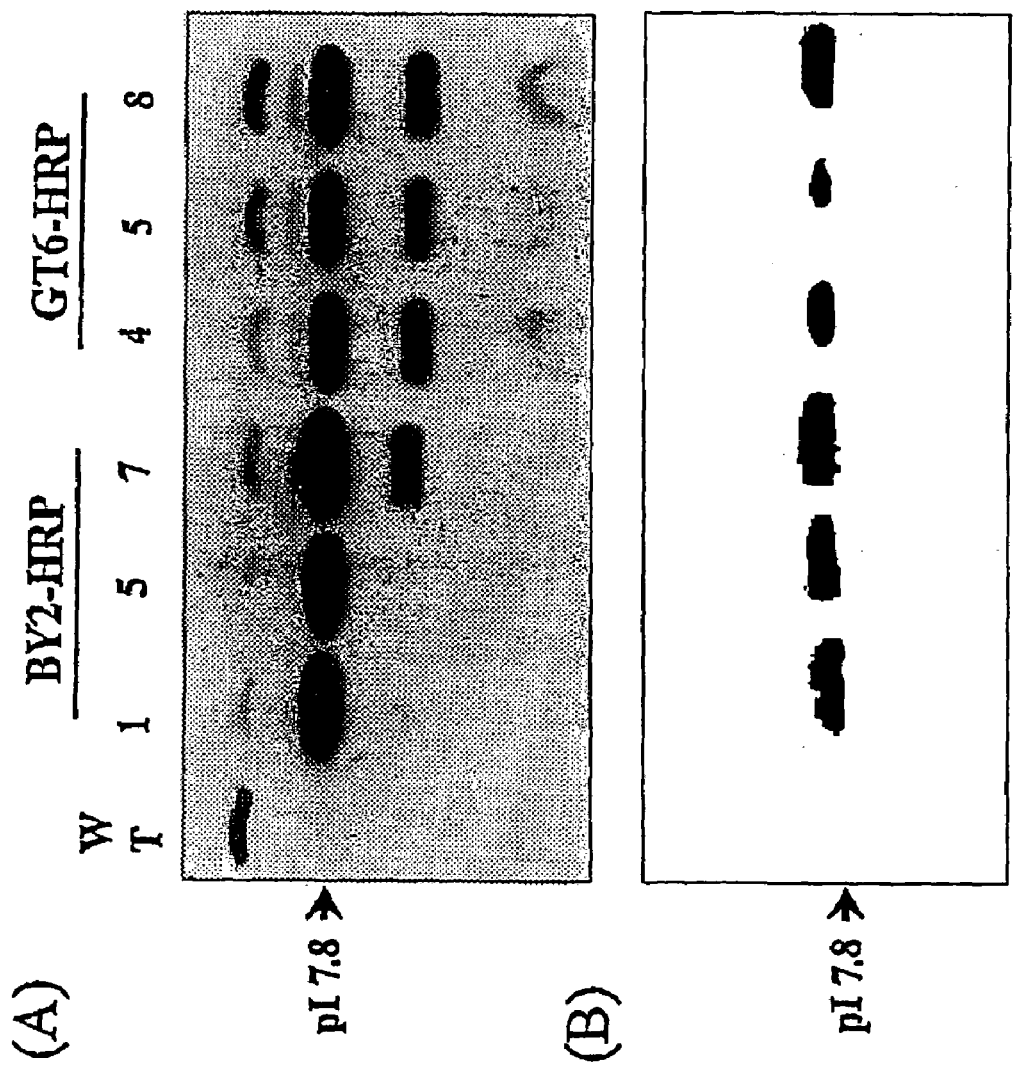
FIG. 10. Photographs of isoelectric focusing and Western blotting which show HRP production in a suspension culture of transgenic cells.

The activity staining of peroxidase was performed according to the method of Sekine et al. (Sekine et al., Plant Cell Technology, 6, 71–75, 1994). As shown in FIG. 10, a significant band not found in wild-type cell line was detected in the pI 7.8 position in the BY2-HRP cell line and the GT6-HRP strain. The results of a Western analysis using anti-HRP antibodies confirmed the detection of a signal at the position corresponding to pI 7.8 and the expression of HRP in the double transformant GT6-HRP with hGT and HRP.

EXAMPLE 6

Structural Analysis of the N-Linked Sugar Chains in the Transformant GT6 Cells (Method Used to Analyze the Sugar Chain Structure)

The N-linked sugar chains in the transformant GT6 cells were analyzed by combining reverse-phase HPLC and size-fractionation HPLC, performing the two-dimensional PA sugar chain mapping, performing exoglycosidase digestion, and when performing ion spray tandem mass spectrometry (IS-MS/MS) (Perkin Elmer Co., Ltd.). First, the cell extract solution was delipidated with acetone, treated with hydrazine for 12 hours at 100° C., and the sugar chain portion was released. The hydrazinolysate was N-acetylated, desalted using the Dowex 50×2 and the Dowex 1×2 (The Dow Chemical Co., Ltd. and its representative in Japan, Muromachi Chemical Industry Co., Ltd.), then fractionized by using 0.1 N ammonia and the Sephadex G-25 gel filtration column (1.8×180 cm) (Pharmacia Co., Ltd.). Pyridylamination was then performed as described above. The pyridylaminated sugar chains (PA sugar chains) were then separated using a Jasco 880-PU HPLC device with a Jasco 821-PP Intelligent Spectrophotometer (Japan Spectroscopic Co., Ltd.) and Cosmosil 5C18-P and Asahipak NH2P-50 columns. The elution positions were compared with a standard either produced by the applicant or purchased (from Wako Pure Chemical Industries, Ltd. and Takara Shuzo Co., Ltd.).

The glycosidase digestion using N-acetyl-β-D-glucosaminidase (*Diplococcus pneumoniae*, Boehringer Mannheim) or mannosidases (Jack bean, Sigma) was performed on about 1 nmol of the PA sugar chains under the same conditions as the method described in Kimura, Y. et al.,: Biosci. Biotech. Biochem. 56 (2), 215–222, 1992. Digestion using β-galactosidase (*Diplococcus pneumoniae*, Boehringer Mannheim) or *Aspergillus saitoi*-derived α-1,2 mannosidase (provided by Dr. Takashi Yoshida at Tohoku University) was performed by adding 1 nmol of PA sugar chains and 200 mU β-galactosidase or 60 µg of α-1,2 mannosidase to 50 mM of sodium acetate buffer (pH 5.5) and incubating at 37° C. After the resultant reaction solution was boiled and the enzyme reaction was stopped, a portion of the digested product was analyzed using size-fractionation HPLC. The molecular weight of the digested product was analyzed using ion spray tandem mass spectrometry (IS-MS/MS) and/or compared to the standard sugar chain as described in Palacpac, N. Q. et al., Biosci. Biotech. Biochem. 63(1) 35–39, 1999 and Kimura, Y. et al., Biosci. Biotech. Biochem. 56 (2), 215–222, 1992.

The IS-MS/MS experiment was performed using a Perkin Elmer Sciex API-III. It was performed in positive mode with an ion spray voltage of 4200 V. Scanning was performed every 0.5 Da, and the m/z was recorded from 200.

(Analysis of the Sugar Chains in the GT6 Cells)

Figure 11:
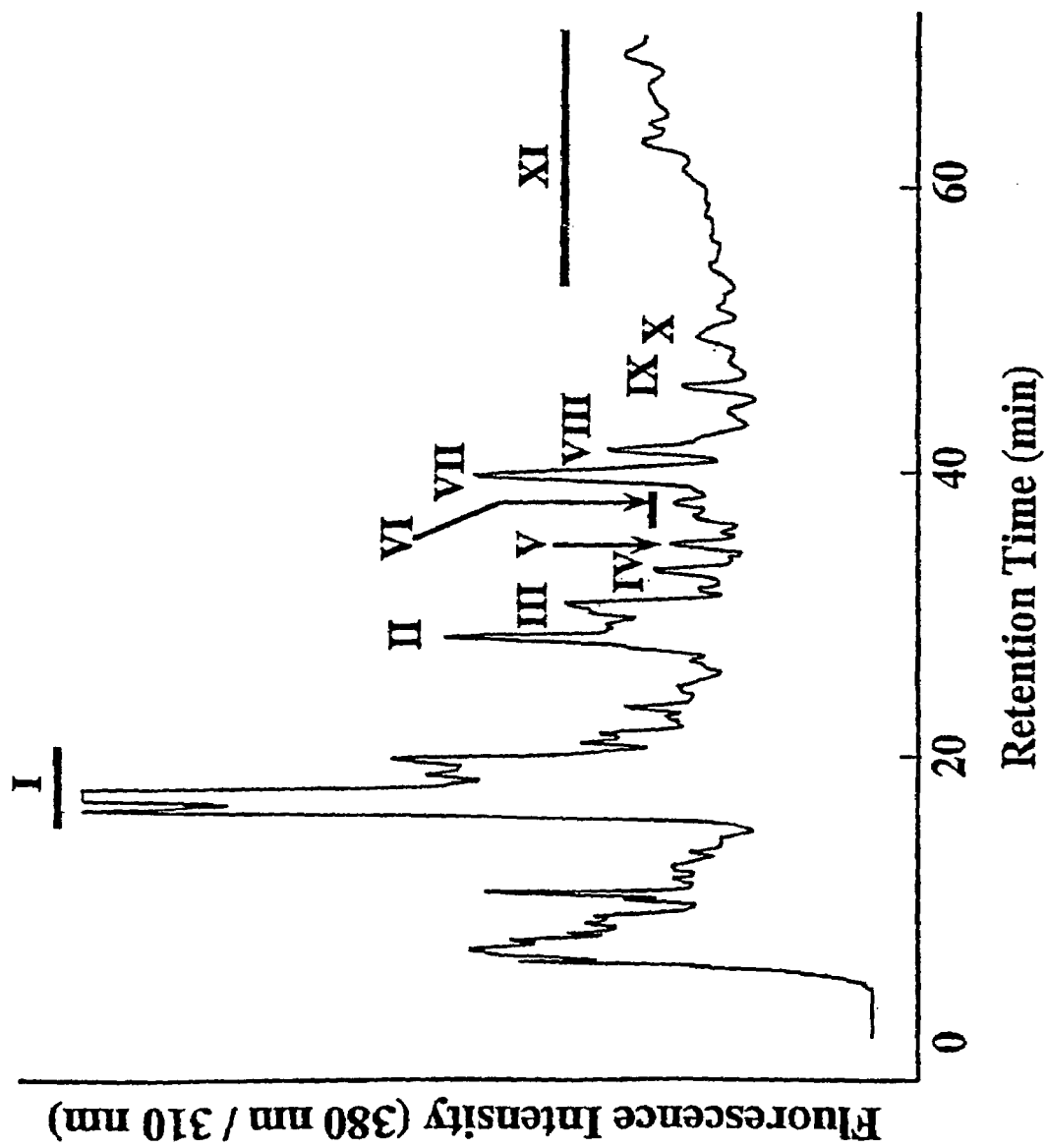
FIG. 11. A graph showing the reverse-phase HPLC pattern of a PA sugar chain eluted in 0–15% acetonitrile linear gradient in 0.02% TFA over 60 minutes and at a flow rate of 1.2 ml/min. I–XI shows the fractions eluted and purified from size-fractionation HPLC. Excitation wavelength and emission wavelength were 310 mm and 380 mm, respectively.
Figure 12:
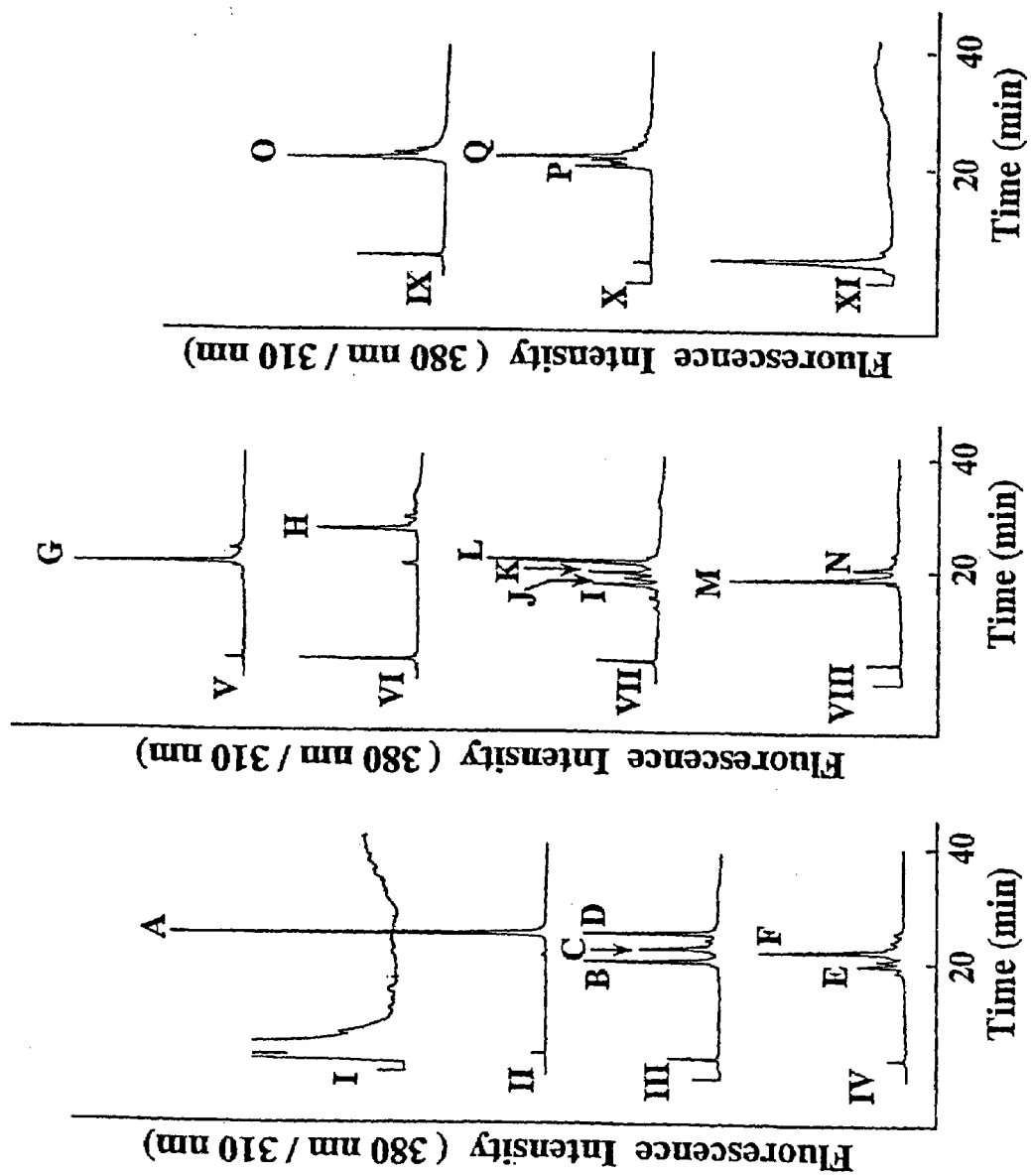
FIG. 12. Graphs showing the size-fractionation HPLC pattern of the PA sugar chain in FIG. 11. Elution was performed in a 30–50% water gradient in the water-acetonitrile mixture over 40 minutes and at a flow rate of 0.8 ml/min. The excitation wavelength and emission wavelength were 310 nm and 380 nm, respectively.

The PA sugar chains prepared from the GT6 cells were purified and analyzed using a combination of reverse-phase HPLC and size-fractionation HPLC. In Fraction I at the 10–20 minute positions in the size-fractionation HPLC (FIG. 11), no N-linked sugar chains were eluted. This suggests that the Fraction I is a non-absorption portion containing by-products of hydrazinolysis. In the MS/MS analysis, no fragment ion with m/z values of 300, which corresponds to PA-GlcNAc, was detected. Similarly, Fraction XI at the 50–60minute positions did not have a peak indicating elution by the size-fractionation HPLC. Therefore, it is clear that there were no N-linked sugar chains. The 17 peaks including A–Q shown in FIG. 12 were all collected and purified after the analysis from Fraction II to Fraction X in the size-fractionation HPLC (FIG. 11) was completed.

The IS-MS/MS analysis found that seven of these peaks were N-linked sugar chains. The following is the result from the analysis of these peaks.

The elution positions and molecular weights of oligosaccharides -A, -E, -H. -I, -M, -O, -P and -Q (FIG. 12) did not correspond to those of PA sugar chain standards. In the MS/MS analysis, the m/z values of 300 and 503, which respectively correspond to PA-GlcNAc and PA-GlcNac$_2$, were detected. However, the fragment ions were not detected corresponding to ManGlcNA$_2$ (M1) or the trimannose core sugar chain Man$_3$GlcNAc$_2$ (M3) which are generally found in N-linked sugar chain (data not shown). Even the oligosaccharides -B, -D and -N at the other peaks did not have fragment ions detected with an m/z value of 300. Thus, these were not N-linked sugar chains. The seven remaining N-linked sugar chains were then examined.

The elution positions and molecular weights of peak-C (m/z 1637.5; molar ratio 9.3%), peak-F ([M+2H] 2+m/z 819.5, [M+H]+m/z 1639; molar ratio 15.9%), and peak-G (m/z 1475.5; molar ratio 19.5%) indicated high mannose-type sugar chains Man$_7$GlcNAC$_2$ (Isomer M7A and M7B) and Man$_6$GlcNAc$_2$ (M6B) respectively. When digested by Jack bean α-mannosidase, it was indicated that the N-linked sugar chains are degraded to ManGlcNAc (M1) by size-fractionation HPLC analysis (data not shown). In an IS-MS experiment on the digestion product, the ion with an m/z value of 665.5 corresponding to a calculated value of 664.66 for M1 was detected, indicating that these N-linked sugar chains have the same structure as respective corresponding PA sugar chain standard.

Peak-J (6.6%) had a molecular weight of 1121.5, which is almost the same as the calculated molecular weight value of m/z 1121.05 of Man$_3$Xyl$_1$GlcNAc$_2$-PA (M3X). The positions of the fragment ions were 989.5, 827.5, 665.5, 503.3 and 300. This does not contradict the findings that Xyl, Man, Man, Man, and GlcNAc were released in successive order from Man$_3$Xyl$_1$GlcNAc$_2$-PA. When digested using Jack bean α-mannosidase, the mannose residues on the non-reducing terminus can be removed, and the two-dimensional mapping revealed the same elution positions as those of Man$_1$Xyl$_1$GlcNAc$_2$-PA (data not shown).

The results of the analysis of the IS-MS experiment on peak-K (13.2%) fraction revealed that this fraction contains two types of N-linked sugar chains, one has the molecular weight of 1314.0 (1.4%) and the other has the molecular weight of 1354.5 (11.8%). This fraction was subjected to reverse-phase HPLC, purified and analyzed. The sugar chain peak K-1 with a molecular weight of 1314.0 had the same two-dimensional mapping and m/z value measured as that of the sugar chain standard Man$_5$GlcNAc$_2$-PA (M5). When treated using jack bean α-mannosidase, the elution positions of the degradated product had shifted to positions similar to those of M1 in the two-dimensional mapping. This indicates the removal of four mannose residues.

(Galactose-Added N-Linked Type Sugar Chains in the GT6 Cells)

Figure 13:
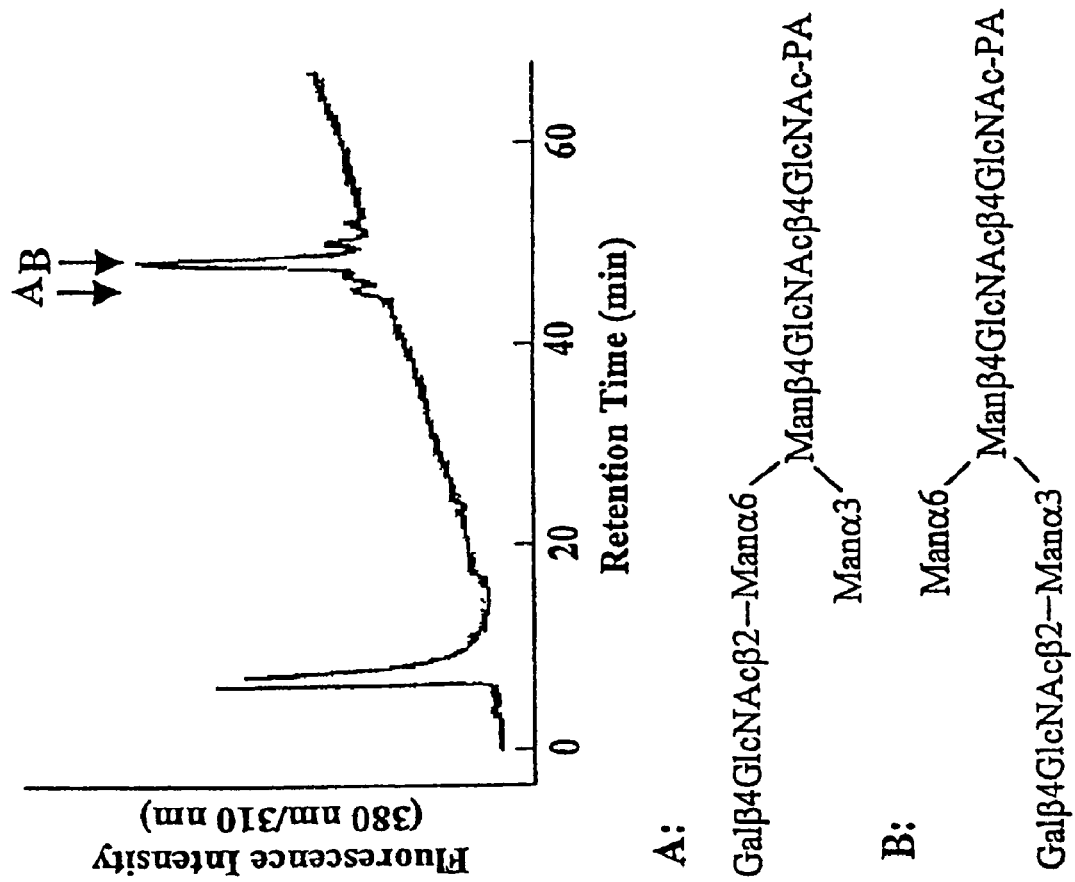
FIG. 13. A graph showing the elution position of peak-K2 on reverse phase HPLC wherein two standard sugar chain products A and B are compared with the peak K2. The elution conditions were the same as in FIG. 11. That is, elution was performed in 0–15% acetonitrile linear gradient in 0.02% TFA over 60 minutes and at a flow rate of 1.2 ml/min.

The determined m/z value of 1354.5 for sugar chain peak K-2 is almost the same as the molecular weight m/z value of 1354.3 predicted for Gal$_1$GlcNAc$_1$Man$_3$GlcNAc$_2$-PA (Gal-GNM3). The result of the mass spectrometry indicated that fragment ions were derived from the parent molecules. The m/z value of 1193.5 indicated GlcNAc$_1$Man$_3$GlcNAc$_2$-PA, the m/z value of 989.5 indicated Man$_3$GlcNAc$_2$-PA, the m/z value of 827.5 indicated Man$_2$GlcNAc$_2$-PA, the m/z value of 665 indicated ManGlcNAc$_2$-PA, the m/z value of 503 indicated GlcNAc$_2$-PA, the m/z value of 336 indicated ManGlcNAc, the m/z value of 300 indicated GlcNAc-PA, and the m/z value of 204 indicated GlcNAc. From the putative N-linked sugar chain structure, it is considered to be either of two GalGNM3 isomers (FIG. 13). It is either Galβ4GlcNAcβ2Manα6 (Manα3)Manβ4GlcNacβ4GlcNAc-PA or Manα6 (Galβ4GlcNAcβ2Manα3)Man β4GlcNAcβ4GlcNAc-PA. The purified PA sugar chains had reverse-phase HPLC elution positions that were the same as the sugar chain standard Manα6 (Galβ4GlcNAcβ2Manα3) Manβ4GlcNAcβ4GlcNAc-PA (FIG. 13B).

Figure 14:
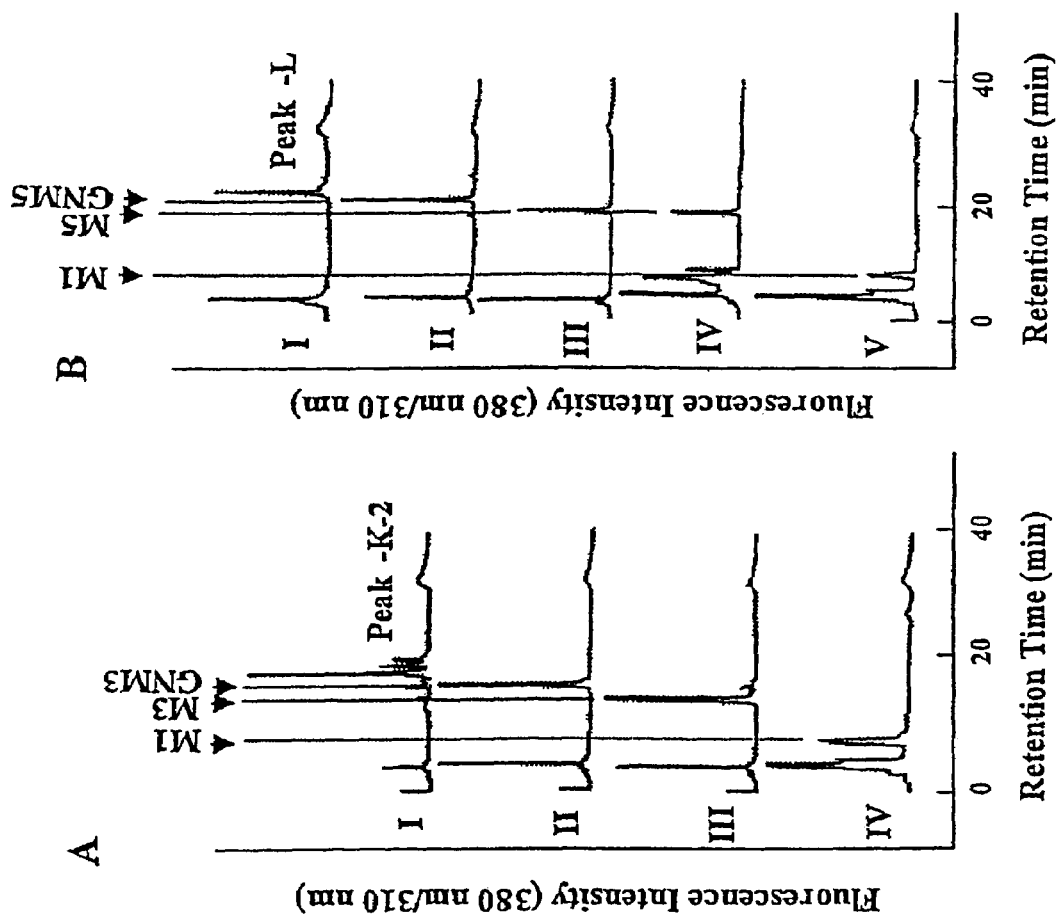
FIG. 14. Graphs showing the SF-HPLC profiles of galactosylated PA sugar chains obtained after exoglycosidase digestion. Elution was performed in a 30–50% water gradient in the water-acetonitrile mixture over 25 minutes and at a flow rate of 0.8 ml/min. (A) PA-sugar chain K-2: I is the elution position of the galactosylated PA sugar chain used; II is β-galactosidase digests of I: III is a N-acetyl-β-D-glucosaminidase digests of II; IV is jack bean α-mannosidase digests of III. (B) PA-sugar chain L: I is the elution position of the galactosylated PA sugar chain used; II is β-galactosidase digests of I; III is N-acetyl-β-D-glucosaminidase digests of II; IV is α1,2 mannosidase digests of III; V is jack bean α-mannosidase digests of III.
Figure 15:
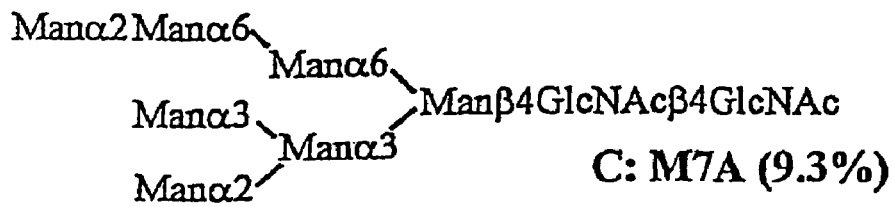
FIG. 15. Estimated structures of the N-linked glycans obtained from the transformed cells. The numbers in the parentheses indicate the molar ratio.
Figure 15:
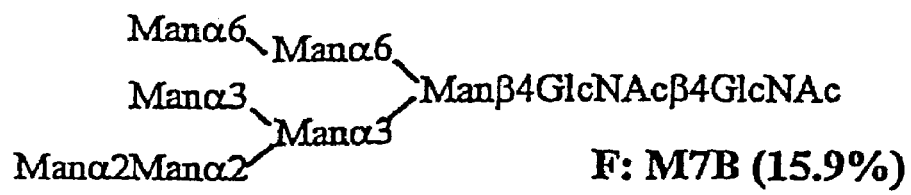
Figure 15:
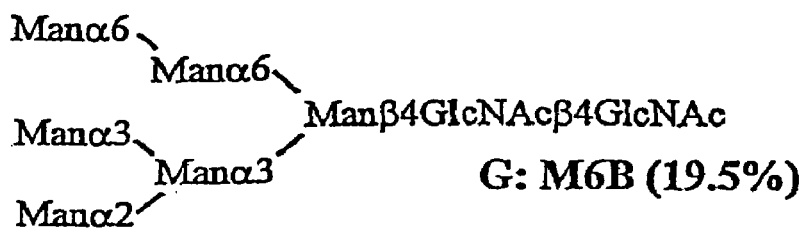
Figure 15:
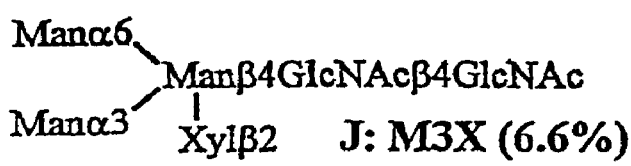
Figure 15:
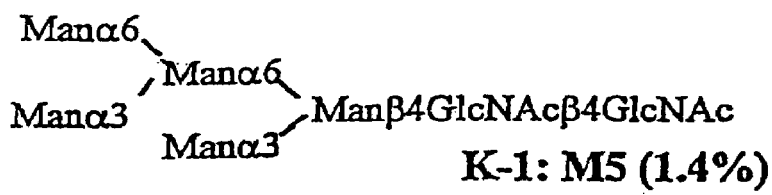
Figure 15:
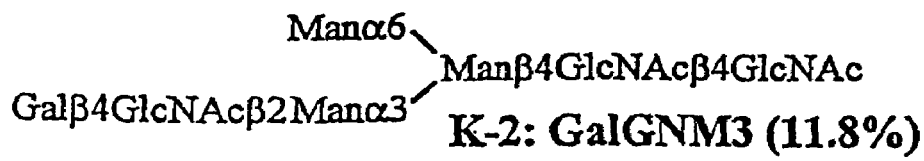
Figure 15:
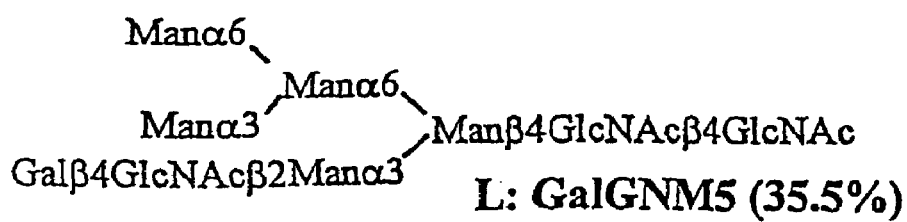

The sugar chain was treated with exoglycosidase and the structure of the sugar chain was verified. The *D. pneumoniae* β-galactosidase is a Gal β1, 4GlcNAc linkage specific enzyme. The digested product of the sugar chain by the enzyme was eluted at the same position as that of the GlcNAc$_1$Man$_3$GlcNAc$_2$-PA in the size-fractionation HPLC (FIG. 14A-II). An m/z of 1192.0 was obtained from the IS-MS/MS analysis. These results indicate a galactose residue has been removed from the GlcNAc on the non-reducing terminus with the β1,4 binding. When the product was digested by a N-acetyl-β-D-glucosaminidase derived from *Diplococcus pneumoniae*, which is β1,2 GlcNAc linkage specific (Yamashita, K. et al., J. Biochem. 93, 135–147, 1983), the digested product was eluted at the same position as that: of the standard Man$_3$GlcNAc$_2$-PA in the size-fractionation HPLC (FIG. 14A-III). When the digested product was treated with jack bean α-mannosidase, it was eluted at the same position as that of the standard ManGlcNAc$_2$-PA in the size-fractionation HPLC (FIG. 14A-IV). The sugar chain structure is shown in K-2 of FIG. 15.

The mass spectroscopy analysis of Peak L(35.5%) gave [M+2H] 2+ of 840, [M+H]+ of 1680.0, which nearly matched the molecular weight m/z value of 1678.55 expected for Gal$_1$GlcNAc$_1$Man$_5$GlcNAc$_2$-PA (GalGNM5). The result of the mass spectrometry indicated fragment ions derived from the parent molecules. The m/z value of 1313.5 indicated Man$_5$GlcNAc$_2$-PA, the m/z value of 1152 indicated Man$_4$GlcNAc$_2$-PA, the m/z value of 989.5 indicated Man$_3$GlcNAc$_2$-PA, the m/z value of 827.5 indicated Man$_2$GlcNAc$_2$-PA, the m/z value of 665 indicated ManGlcNAc$_2$-PA, the m/z value of 503 indicated GlcNAc$_2$-PA, the m/z value of 336 indicated ManGlcNAc, the m/z value of 300 indicated GlcNAc-PA, and the m/z value of 204 indicated GlcNAc. The product digested with *D. pneumoniae* β-galactosidase was eluted at the same position as that of GlcNAc$_1$Man$_5$GlcNAc$_2$-PA in the size-fractionation HPLC (FIG. 14B-II). The results indicate that a galactose residue is bound to the GlcNAc on the non-reducing terminus with the β1,4 linkage. The removal of the galactose was confirmed by the molecular weights obtained from the IS-MS/MS analysis. [M+2H] 2+ was 759 and [M+H] was 1518.0. The mass spectrometry indicated fragments ions derived from the GlcNAc$_1$Man$_5$GlcNAc$_2$-PA with a parent signal of m/z 1518.0. The m/z value of 1314 indicated Man$_5$GlcNAc$_2$-PA, the m/z value of 1152 indicated Man$_4$GlcNAc$_2$-PA, the m/z value of 990 indicated Man$_3$GlcNAc$_2$-PA, the m/z value of 827.5 indicated Man$_2$GlcNAc$_2$-PA, the m/z value of 665.5 indicated Man$_1$GlcNAc$_2$-PA, the m/z value of 503 indicated GlcNAc$_2$-PA, and the m/z value of 300 indicated GlcNAc-PA. When the GlcNAc$_1$Man$_5$GlcNAc$_2$-PA was digested with an N-acetyl-β-D-glucosaminidase derived from *Diplococcus pneumoniae*, the digested product was eluted at the same position as that of the standard Man5GlcNAc$_2$-PA in the size-fractionation HPLC (FIG. 14B-III). Even when treated with α-1,2 mannosidase derived from *Aspergillus saitol*, the elution position did not shift (FIG. 14B-IV). However, when treated with jack bean α-mannosidase, it was eluted at the same position as that of standard Man$_1$GlcNAc$_2$-PA in the size-fractionation HPLC (FIG. 14B-V). This indicates the removal of four mannose residues in the non-reducing terminus. These results indicate that in the PA sugar chain, none of five mannose residues are α1,2 linked to the mannose residue which are α1,3 binding. The exoglycosidase digestion, two-dimensional sugar chain mapping, and IS-MS/MS analysis indicate a sugar chain structure of GalGNM5 as shown by L in FIG. 15.

Figure 20:
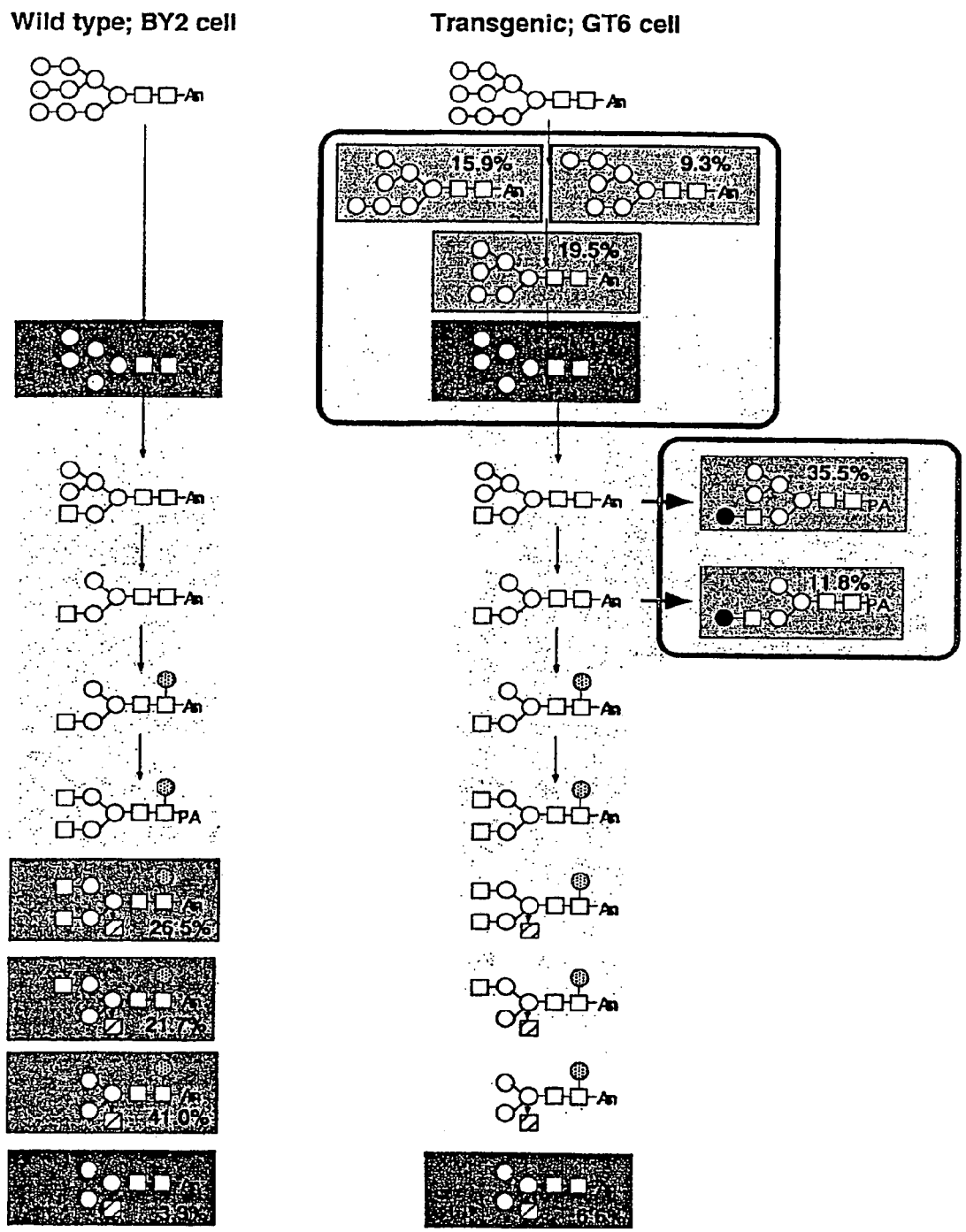
FIG. 20. Structures of N-linked glycans and the ratio of each N-linked glycan in GT6 cell line along with those in wild-type BY2 cell line determined similarly. □ denotes GlcNAc, ○ denotes mannose, ◖ denotes galactose, and ■ denotes sialic acid, respectively.

FIG. 20 summarizes the above results regarding the structure of N-linked glycans and the ratio of each N-linked glycan in GT6 cell line along with those in wild-type BY2 cell line determined similarly. In FIG. 20, □ denotes GlcNAc, ○ denotes mannose, ● denotes galactose, □ with hatched lines therein denotes xylose, and ○ with dots therein denotes fucose respectively.

Figure 21:
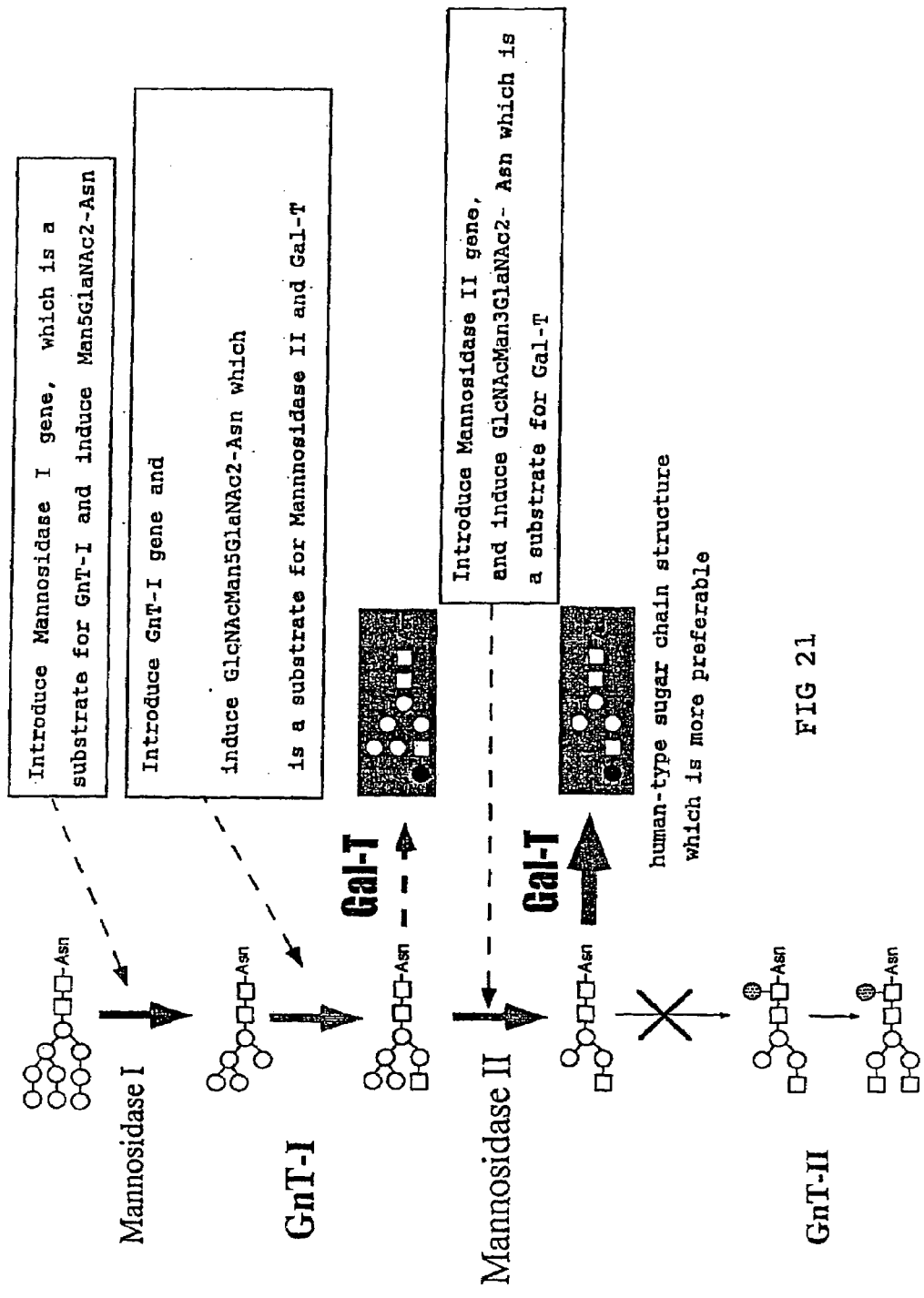
FIG. 21 illustrates one of the embodiment of the present invention. In GT6 cell line, the isomers Man7-, Man6- and Man5GlcNAc2 were observed. Because those high-mannose type oligosaccharides will be converted by some glycan processing enzymes to be substrates for β1,4-galactosyltransferase (Gal T), introduction of GlcNAc I, Man I and Man II cDNAs could more efficiently lead the oligosaccharide Man7-5GlcNAc2 to GlcNAcMan3GlcNAc2, which can be a substrate of GalT.

In GT6 cell line, the isomers Man7-, Man6- and Man5GlcNAc2 were observed. Because those high-mannose type oligosaccharides will be substrates for β1,4-galactosyltransferase (Gal T), introduction of GlcNAc I, Man I and Man II cDNAs can more efficiently lead the oligosaccharide Man7-5GlcNAc2 to GlcNAcMan3GlcNAc2, which can be a substrate of GalT (FIG. 21).

A. thaliana cg1I mutant, that lacks GnT I, can not sythesize complex type N-glycans (von Schaewen, A., Sturm, A., O'Neill, J., and Chrispeels, M J., Plant Physiol., August 1993 August; 102(4):1109–1118, Isolation of a mutant *Arabidopsis* plant that lacks N-acetyl glucosaminyl transferase I and is unable to synthesize Golgi-modified complex N-linked glycans). Complementation with the human GnT I in the cg1I mutant indicated that the mammalian enzyme could contribute the plant N-glycosylation pathway (Gomez, L. and Chrispeels, M. J., Proc. Natl. Acad. Sci. USA 1994 Mar. 1; 91(5):1829–1833, Complementation of an *Arabidopsis thaliana* mutant that lacks complex asparagine-linked glycans with the human CDNA encoding N-acetylglucosaminyltransferase I.) Furthermore, GnT I cDNA isolated from *A. thaliana* complemented N-acetylglucosaminyltransferase I deficiency of CHO Lec1 cells (Bakker, H., Lommen, A., Jotdi, W., Stiekema, W., and Bosch, D., Biochem. Biophys. Res. Commun., 1999 Aug. 11; 261(3):829–32, An *Arabidopsis thaliana* cDNA complements the N-acetylglucosaminyltransferase I deficiency of CHO Lec1 cells). cDNAs encoding human Man I and Man II were isolated and sequenced (Bause, E., Bieberich, E., Rolfs, A., Volker, C. and Schmidt, B., Eur J Biochem Oct. 15, 1993 ;217(2):535–40, Molecular cloning and primary structure of Man9-mannosidase from human kidney; Tremblay, L. O., Campbell, Dyke, N. and Herscovics, A., Glycobiology 1998 June; 8(6):585–95, Molecular cloning, chromosomal mapping and tissue-specific expression of a novel human alpha 1,2-mannosidase gene involved in N-glycan maturation; and Misago. M., Liao, Y. F., Kudo, S., Eto, S., Mattei, M. G., Moremen, K. W., Fukuda M. N., Molecular cloning and expression of cDNAs encoding human alpha-mannosidase II and a previously unrecognized alpha-mannosidase IIx isozyme). Human Man I has two isozymes, Man IA and Man IB, and the nucleotide structure of isozymes' cDNA was shown (Bause, E., et al., and Tremblay, L. O., supra).

Figure 22:
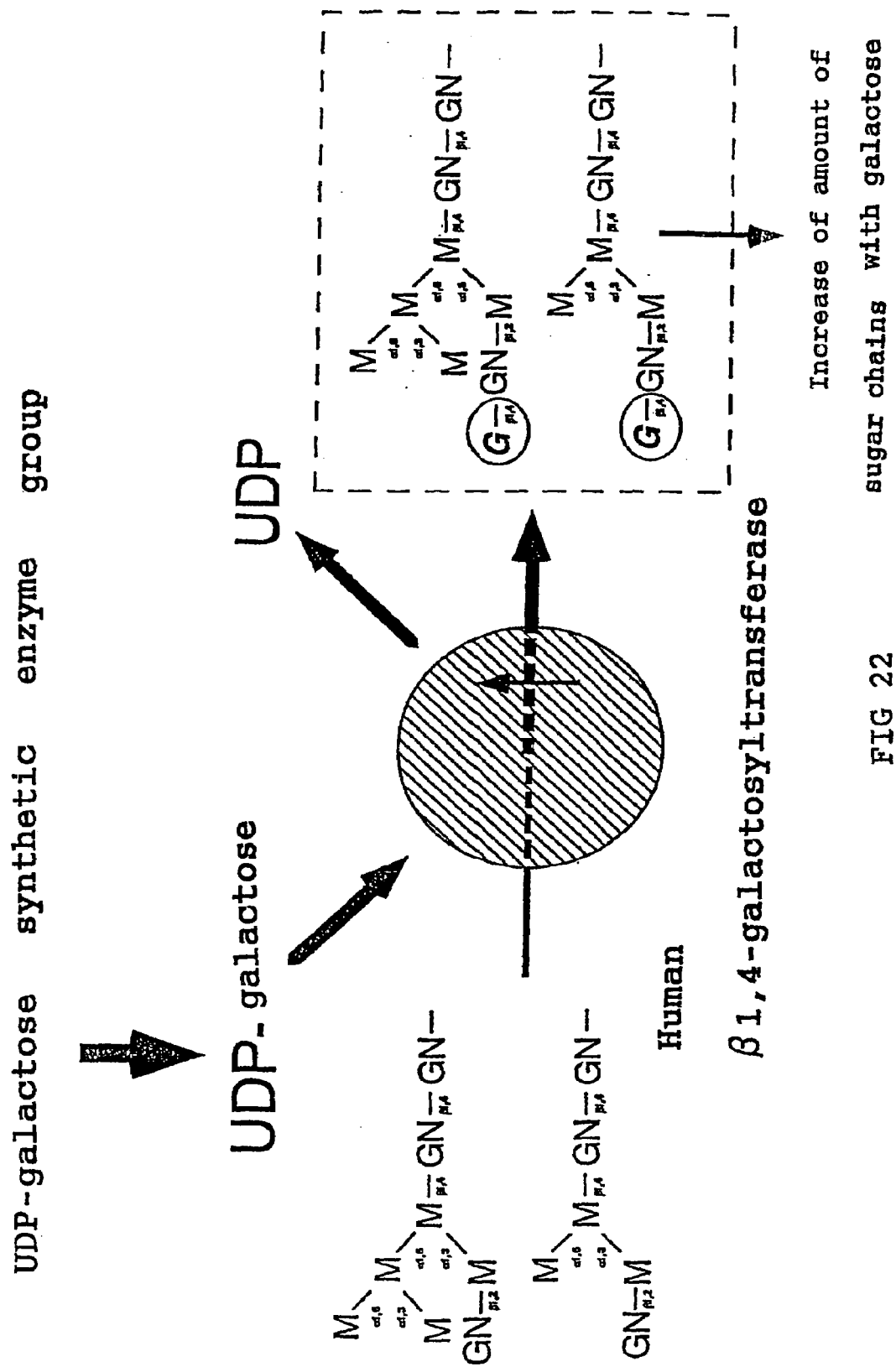
FIG. 22 also illustrates another the embodiment of the present invention. 1,4-Galactosyltransferase (Gal T) uses UDP-galactose as a donor substrate and GlcNAc2Man3GlcNAc2 as an acceptor substrate. Efficient supply of UDP-galactose will enhance the Gal T enzyme reaction and more galactosylated oligosaccharide will be produced.

By transforming these cDNAs into the BY cell line, an efficient cell line producing human-type glycoprotein, can be obtained. β1,4-Galactosyltransferase (Gal T) uses UDP-galactose as a donor substrate and GlcNAc2Man3GlcNAc2 as an acceptor substrate. Efficient supply of UDP-galactose will enhance the Gal T enzyme reaction, and more galactosylated oligosaccharide will be produced (FIG. 22).

EXAMPLE 7

Structural Analysis of the Sugar Chains on the HRP in the Double Transformant GT6-HRP Cells A crude cell lysate was obtained from the homogenate of 50 g of cultured GT6-HRP cells or control BY2-HRP cells grown for seven days, respectively. This crude cell lysate solution was applied to a CM Sepharose FF column (1×10 cm) (Pharmacia Co., Ltd.) equilibrated with 10 mM of sodium phosphate buffer (pH 6.0). After washing the column, the eluted peroxidase was measured at an absorbance of 403 nm. The pooled fraction was concentrated using an ultrafilter (molecular weight cut off: 10,000, Advantec Co., Ltd.), dialyzed against 50 mM of a sodium phosphate buffer (pH 7.0), and then applied to an equilibrated benzhydroxaminic acid-agarose affinity column (1×10 cm) (KemEn Tech, Denmark). After the column was washed in 15 volumes of 50 mM of sodium phosphate buffer (pH 7.0), the absorbed HRP was eluted using 0.5 M boric acid prepared in the same buffer. The peroxidase active fraction obtained was then pooled, dialyzed, and concentrated.

The purified HRP prepared from the double transformant GT6-HRP cells or BY2-HRP cells was applied to a 1×10 cm $RCA_{120}$-agarose column. The column was then washed with 15 volumes of 10 mM ammonium acetate (pH 6.0). The absorbed proteins were then eluted and assayed using conventional methods.

Figure 16:
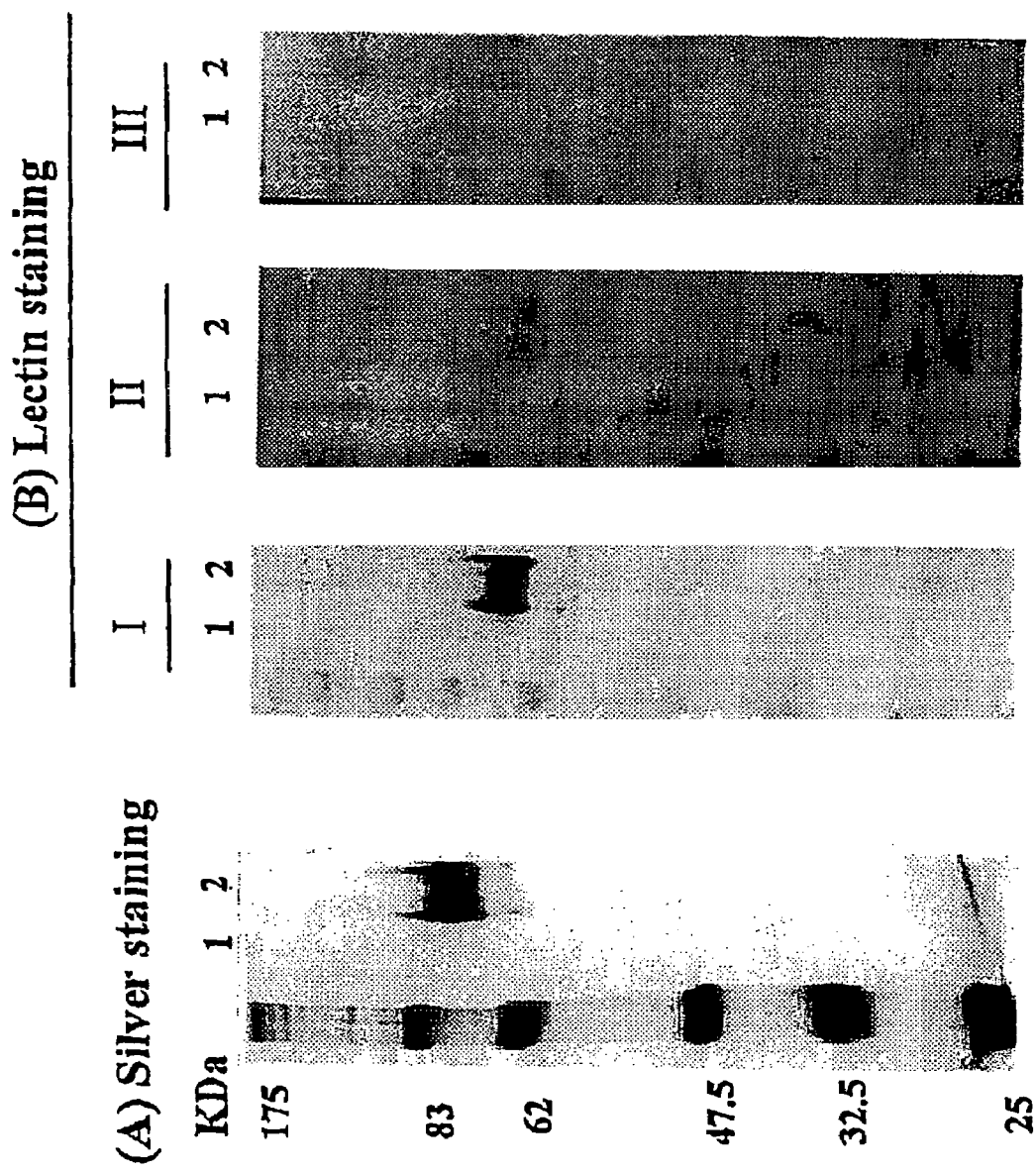
FIG. 16. Photographs of *Ricinus communis* 120 agglutinin ($RCA_{120}$) affinity chromatography showing the detection of glycosylated HRP.

Lectin staining was then performed on the purified HRP eluted from $RCA_{120}$ affinity chromatography whose specificity is specific to β1,4 linkage galactose. The lectin $RCA_{120}$ was bound to only the HRP produced by the transformed cell GT6-HRP. Because the lectin binding was dramatically reduced by preincubation with the galactose which can compete with the lectin (FIG. 16b-III), the binding is carbohydrate specific. Even when the purified HRP is pre-treated with *D. pneumoniae* β-galactosidase, the $RCA_{120}$ binding was inhibited. These results indicate RCA bound specifically to β1,4-linked galactose at the non-reducing end of N-linked glycan on HRP. The absence of RCA-bound glycoproteins in the BY2-HRP cells indicates that these cells can not transfer the β1,4 linked galactose residue to the non-reducing terminus of the HRP glycan.

Figure 17:
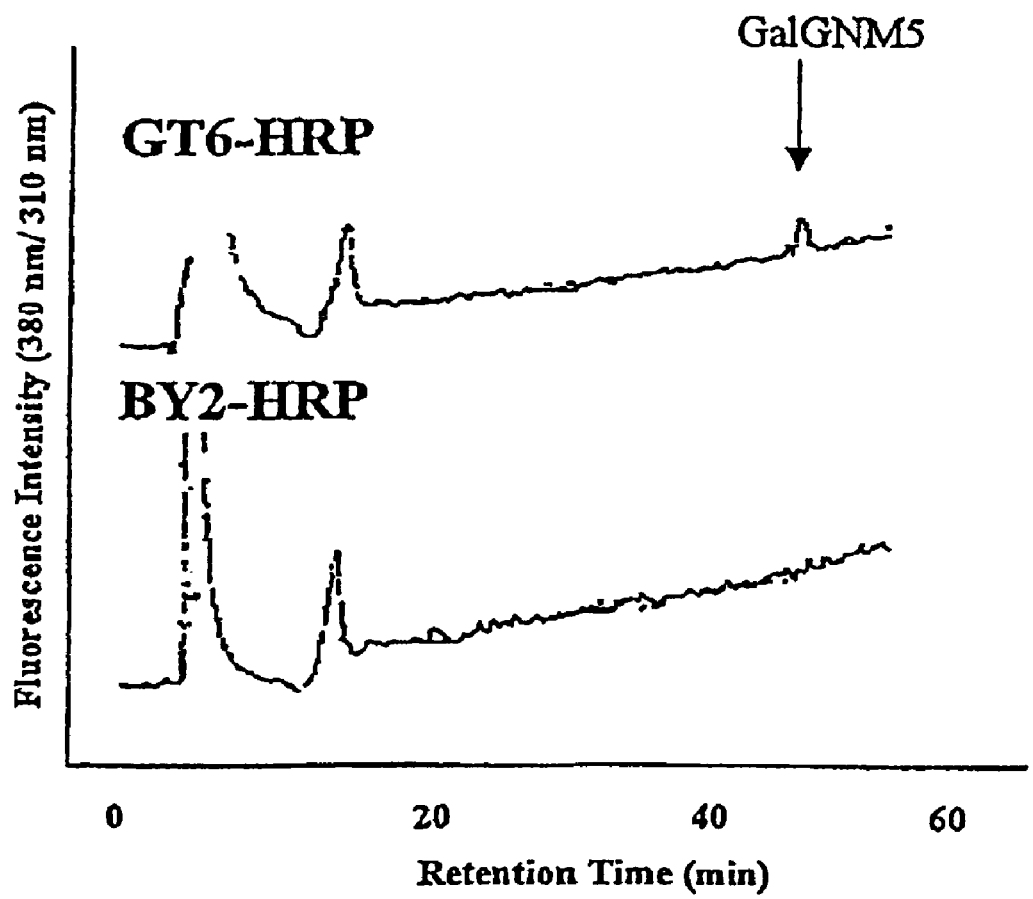
FIG. 17. A graph showing the results of reverse-phase HPLC of the PA sugar chains from purified HRP after $RCA_{120}$ affinity chromatography.

Reverse-phase HPLC of PA derivatives derived from HRP purified using $RCA_{120}$ indicated that the sugar chains on the HRP proteins purified from the GT6-HRP appear as a single peak (FIG. 17). In the reverse phase HPLC, a Cosmosil 5C18-P column or Asahipak NH2P column was used in a Jasco 880-PU HPLC device with a Jasco 821-FP Intelligent Spectrofluorometer. Neither bound proteins nor detectable peaks were observed in the HRP fractions purified from BY2-HRP. The peak obtained from the GT6-HRP in the size-fractionation chromatography was homogenous. The two-dimensional mapping analysis of the peak and chromatography of the peak at the same time with standard sugar chain indicated that the oligosaccharide contained in the peak was $Gal_1GlcNAc1Man_5GlcNAc_2$-PA. The confirmation of this structure was provided using continuous exoglycosldase digestion. The standard sugar chains used were a sugar chains prepared previously (Kimura, Y. et al., Biosci. Biotech. Biochem. 56 (2), 215–222, 1992) or purchased (Wako Pure Chemical, Industries, Ltd. Osaka and Takara Shuzo Co., Ltd.).

The PA sugar chain digested with β-galactosidase (*D. pneumoniae*) matched the elution position of the standard $GlcNAclMan_5GlcNAc_2$-PA indicating the removal of a galactose residue β1,4-linked to a non-reducing terminal GlcNAc. Further digestion with *D. pneumoniae* N-acetyl-β-D-glucosaminidase of β-galactosidase-digested products produced a sugar chain equivalent which is eluted at the same elution position of $Man_5GlcNAc_2$-PA, indicating the removal of a GlcNAc residue β1,2 linked to a non-reducing terminal mannose residue. The removed GlcNAc residue is believed to be linked to α1,3 mannose linked to a β1,4 mannose residue in view of the N-linked type processing route of the plant. In order to confirm the linkage position of the GlcNAc residue, $Man_5GlcNAc_2$-PA (M5) was incubated with α1,2 mannosidase derived from *Aspergillus saitoi*. As expected, an elution position shift was not detected, confirming M5 has the structure Manα1-6(Manα1,3) Manα1-6 (Man α1,3) Manβ1,4GlcNAcβ1,4GlcNAc as predicted. When the sugar chain was digested using jack bean α-mannosidase, it was eluted at the same elution positions of known $Man_1GlcNAc_2$-PA. Therefore, the sugar chain structure corresponded to Manα1-6(Man α1,3)Manα1-6(Gal β1,4GlcNAcβ1,2Manα1,3)Man β1,4GlcNAcβ1,4GlcNAc ($Gal_1GlcNAc_1Man_5GlcNA_2$). These results indicate that the sugar chain in GT6 cell has the structure shown in FIG. 15 and that the sugar chain structure on an HRP protein derived from the double transformant GT6-HRP is Man α1-6(Man α1,3)Man α1-6(Galβ1,4GlcNAcβ1,2Manα1,3)Man β1,4GlcNAc β1,4GlcNAc ($Gal_1GlcNAc_1Man_5GlcNA_2$).

Figure 18:
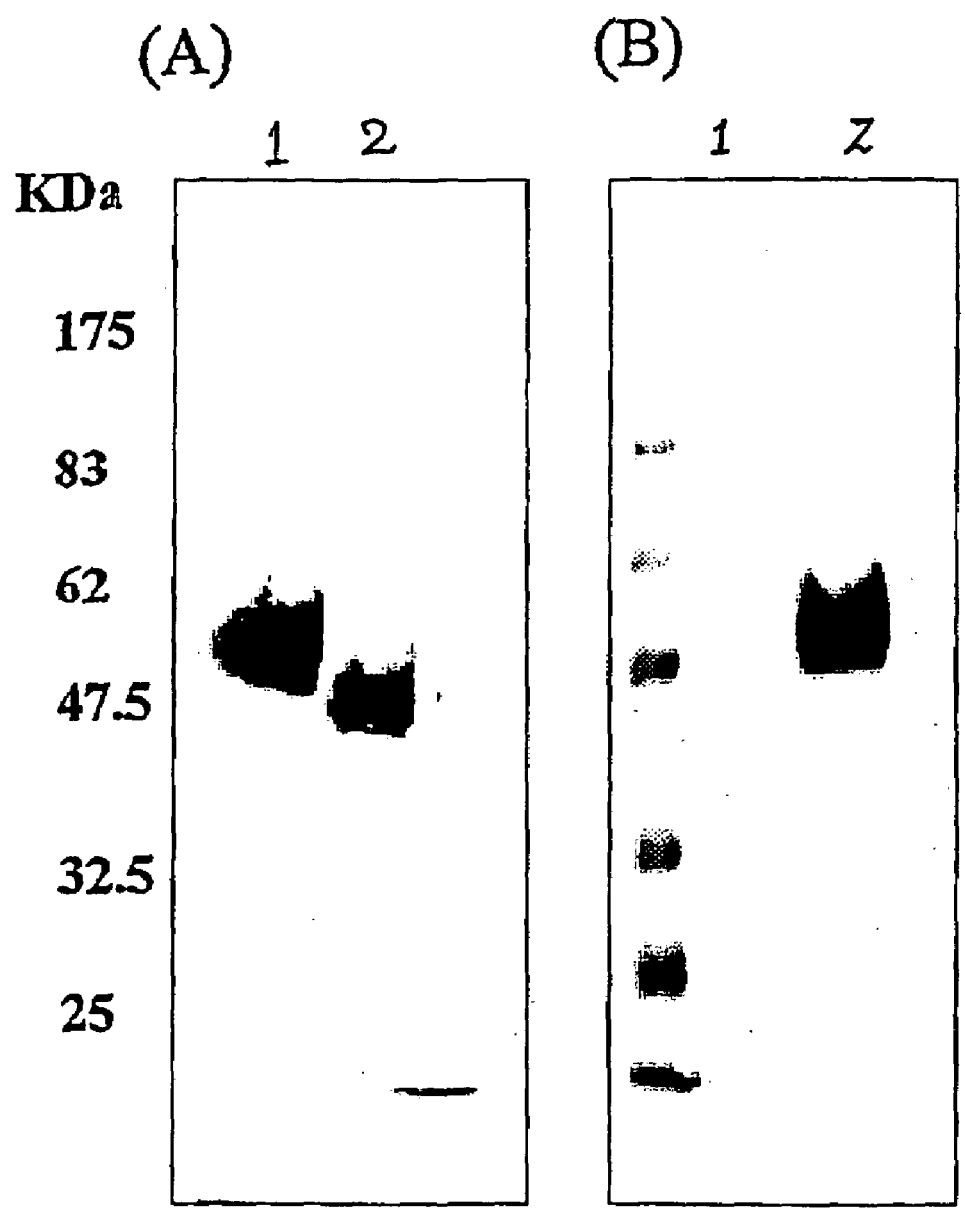
FIG. 18. Photographs of Western blotting showing immune detection of plant specific complex-type glycans. The purified HRP is fractioned by SDS-PAGE, transferred to nitrocellulose, and confirmed with rabbit anti-HRP (A) and an antiserum which is specific for complex-type glycans of plants (B). Lane 1=galactosylated HRP from GT6-HRP after $RCA_{120}$ affinity chromatography; Lane 2=purified HRP from BY2-HRP. The position of the molecule size marker is shown to the left in KDa. The galactosylated N-glycan on HRP derived from the transformant GT6-HRP cells did not react with an antiserum which has been shown to specifically react with β1,2 xylose residue indicative of plant N-glycans.
Figure 19:
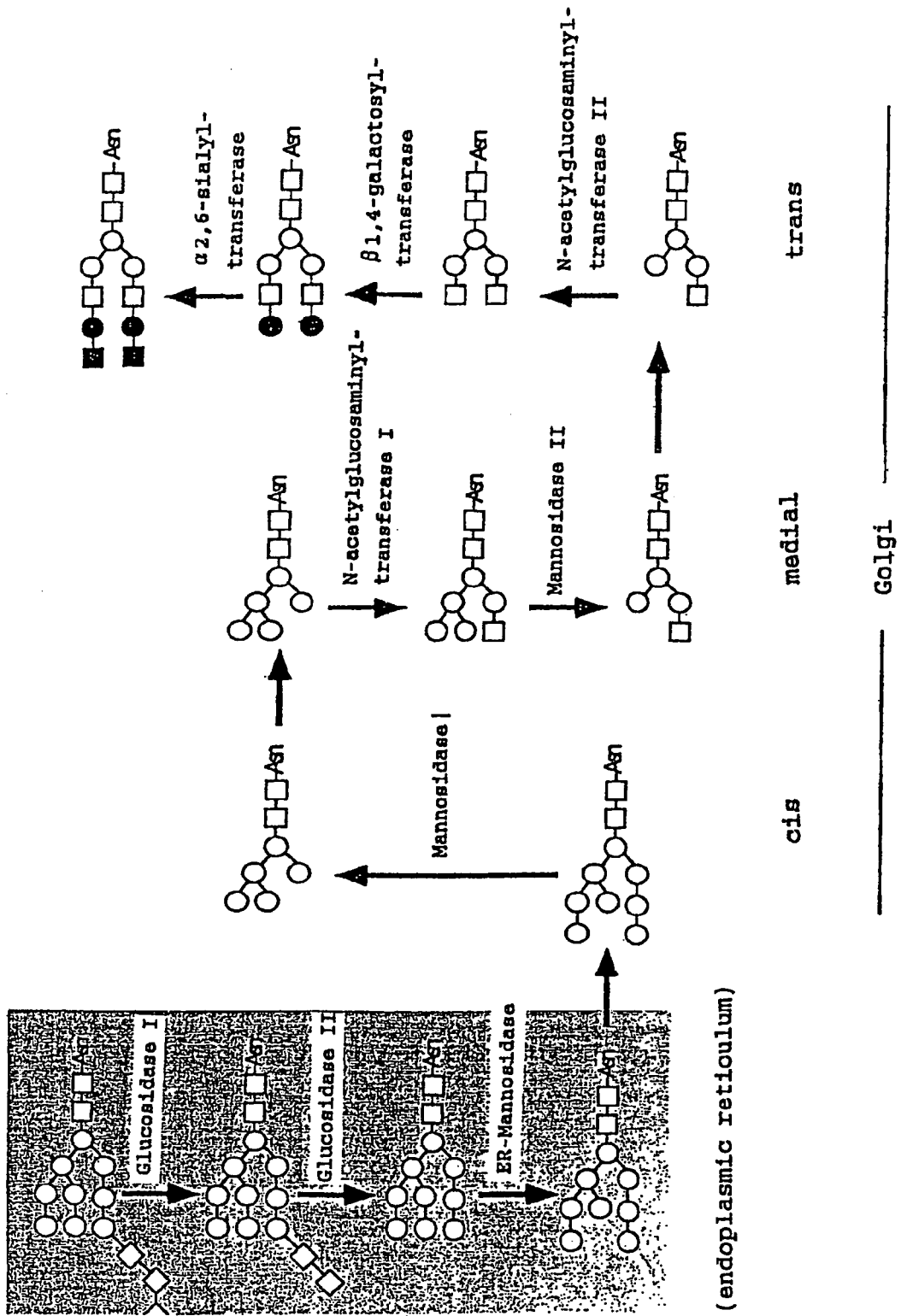
FIG. 19. Structures of N-linked glycans and enzymes involved in the sugar chain modification pathway in Endoplasmic reticulum and Goldi bodies. ◇ denotes glucose, □ denotes GlcNAc, ○ denotes mannose, ● denotes galactose, and ■ denotes sialic acid, respectively.

Similarly, the galactosylated N-glycan on HRP derived from the transformant GT6-HRP cells did not react with an antiserum which has been shown to specifically react with β1,2 xylose residue indicative of plant N-glycans. This indicates that one of the sugar residues shown to be antigenic in complex plant glycan, i.e., xylose residue, is not present (Garcia-Casado, G. et al., Glycobiology 6 (4): 471,477, 1996) (FIG. 18).

INDUSTRIAL APPLICABILITY

The present invention provides a method for manufacturing a glycoprotein with a human-type sugar chain. It also provides plant cells that have a sugar chain adding mechanism able to perform a reaction in which a galactose residue is transferred to a acetylglucosamine residue on the non-reducing terminal, wherein the sugar chain adding mechanism is capable of joining a sugar chain which contains a core sugar chain and an outer sugar chain, wherein the core sugar chain consists essentially of a plurality of mannose and acetylglucosamine, and the outer sugar chain contains a terminal sugar chain portion containing a galactose on the non-reducing terminal. The present invention further provides a glycoprotein with a human-type sugar chain obtained by the present invention. A glycoprotein with a mammalian, e.g., human-type sugar chain of the present invention is not antigenic because the glycosylation is a human-type. Therefore, it can be useful for administering to animals including humans.

The invention claimed is:

1. A plant-produced glycoprotein having a human-type sugar chain, obtained from a transformed plant cell, wherein the transformed plant cell was produced by: introducing to a plant cell a gene encoding a galactosyltransferase enzyme and a gene of an exogenenous glycoprotein; cultivating the transformed plant cell; and when desired separating the resulting glycoprotein.

2. The glycoprotein according to claim 1, wherein the galactosyltransferase enzyme transfers a galactose residue to a non-reducing terminal acetylglucosamine residue.

3. The glycoprotein according to claim 1, wherein the glycoprotein with a human-type sugar chain comprises a core sugar chain and an outer sugar chain, wherein the core sugar chain comprises a plurality of mannose and acetylglucosamine, and wherein the outer sugar chain contains a terminal sugar chain portion with a non-reducing terminal galactose.

4. The glycoprotein according to claim 3, wherein the outer sugar chain has a straight chain configuration.

5. The glycoprotein according to claim 3, wherein the outer sugar chain has a branched chain configuration.

6. The glycoprotein according to claim 5, wherein the branched sugar chain portion has a mono-, bi-, tri, or tetra-configuration.

7. The glycoprotein according to claim 3, wherein the glycoprotein produced contains no fucose or xylose linked to one or more of the core sugar chain, the outer sugar chain and the terminal sugar chain.

8. The glycoprotein according to claim 1 wherein the gene encoding an exogenous glycoprotein is selected from one or more of the group consisting of enzymes, hormones, cytokines, antibodies, vaccines, receptors and serum proteins.

9. The glycoprotein according to claim 8, wherein the exogenous glycoprotein encoded by the introduced gene is an enzyme selected from one or more of the group consisting of horseradish peroxidase, kinase, glucocerebrosidase, α-galactosidase, tissue-type plasminogen activator (TPA), and 3-hydroxy-3-methylglutaryl coenzyme A (HMG-CoA) reductase.

10. The glycoprotein according to claim 8, wherein the exogenous glycoprotein encoded by the introduced gene is a hormone or cytokine selected from one or more of the group consisting of enkephalin, interferon-alpha, granulocyte-macrophage colony stimulating factor (GM-CSF), granulocyte colony stimulating factor (C-CSF), chorion stimulating hormone, interleukin-2, interferon-beta, interferon-gamma, erythropoietin, vascular endothelial growth factor, human choriogonadotropin (HCG), leuteinizing hormone (LH), thyroid stimulating hormone (TSH), prolactin, and ovary stimulating hormone.

11. The glycoprotein according to claim 8, wherein the exogenous glycoprotein encoded by the introduced gene is an antibody selected from immunoglobulin G (IgG) or single chain variable region antibody fragments (scFV).

12. The glycoprotein according to claim 1 or 3 wherein the sugar chain is a human-type sugar chain.

13. A plant-produced glycoprotein comprising no fucose or xylose linked to one or more of the core sugar chain, the outer sugar chain and the terminal sugar chain.

* * * * *

SEQUENCE LISTING

```
<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:primer
      hGT-5Eco

<400> SEQUENCE: 1
aaagaattcg cgatgccagg cgcgcgtccc t                              31

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:primer
      hGT-2Sal

<400> SEQUENCE: 2
tcgatcgcaa aaccatgtgc agctgatg                                  28

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:primer
      hGT-7Spe

<400> SEQUENCE: 3
acgggactcc tcaggggcga tgatcataa                                 29

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:primer
      hGT-6Spe

<400> SEQUENCE: 4
aagactagtg ggccccatgc tgattga                                   27

<210> SEQ ID NO 5
<211> LENGTH: 1158
<212> TYPE: DNA
```

```
<213> ORGANISM: Homo sapiens
<220> FEATURE:
<221> NAME/KEY: CDS
<222> LOCATION: (1)..(1155)

<400> SEQUENCE: 5 atg cca ggc gcg tcc cta cag cgg gcc tgc cgc ctg ctc gtg gcc gtc      48
Met Pro Gly Ala Ser Leu Gln Arg Ala Cys Arg Leu Leu Val Ala Val
 1               5                  10                  15 tgc gct ctg cac ctt ggc gtc acc ctc gtt tac tac ctg gct ggc cgc      96
Cys Ala Leu His Leu Gly Val Thr Leu Val Tyr Tyr Leu Ala Gly Arg
             20                  25                  30 gac ctg agc cgc ctg ccc caa ctg gtc gga gtc tcc aca ccg ctg cag     144
Asp Leu Ser Arg Leu Pro Gln Leu Val Gly Val Ser Thr Pro Leu Gln
         35                  40                  45 ggc ggc tcg aac agt gcc gcc gcc atc ggg cag tcc tcc ggg gag ctc     192
Gly Gly Ser Asn Ser Ala Ala Ala Ile Gly Gln Ser Ser Gly Glu Leu
     50                  55                  60 cgg acc gga ggg gcc cgg ccg ccg cct cct cta ggc gcc tcc tcc cag     240
Arg Thr Gly Gly Ala Arg Pro Pro Pro Pro Leu Gly Ala Ser Ser Gln
 65                  70                  75                  80 ccg cgc ccg ggt ggc gac tcc agc cca gtc gtg gat tct ggc cct ggc     288
Pro Arg Pro Gly Gly Asp Ser Ser Pro Val Val Asp Ser Gly Pro Gly
                 85                  90                  95 ccc gct agc aac ttg acc tcg gtc cca gtg ccc cac acc acc gca ctg     336
Pro Ala Ser Asn Leu Thr Ser Val Pro Val Pro His Thr Thr Ala Leu
             100                 105                 110 tcg ctg ccc gcc tgc cct gag gag tcc ccg cta cta gtg ggc ccc atg     384
Ser Leu Pro Ala Cys Pro Glu Glu Ser Pro Leu Leu Val Gly Pro Met
         115                 120                 125 ctg att gag ttt aac atg cct gtg gac ctg gag ctc gtg gca aag cag     432
Leu Ile Glu Phe Asn Met Pro Val Asp Leu Glu Leu Val Ala Lys Gln
     130                 135                 140 aac cca aat gtg aag atg ggc ggc cgc tat gcc ccc agg gac tgc gtc     480
Asn Pro Asn Val Lys Met Gly Gly Arg Tyr Ala Pro Arg Asp Cys Val
145                 150                 155                 160 tct cct cac aag gtg gcc atc atc att cca ttc cgc aac cgg cag gag     528
Ser Pro His Lys Val Ala Ile Ile Ile Pro Phe Arg Asn Arg Gln Glu
                165                 170                 175 cac ctc aag tac tgg cta tat tat ttg cac cca gtc ctg cag cgc cag     576
His Leu Lys Tyr Trp Leu Tyr Tyr Leu His Pro Val Leu Gln Arg Gln
            180                 185                 190 cag ctg gac tat ggc atc tat gtt atc aac cag gcg gga gac act ata     624
Gln Leu Asp Tyr Gly Ile Tyr Val Ile Asn Gln Ala Gly Asp Thr Ile
        195                 200                 205 ttc aat cgt gct aag ctc ctc aat gtt ggc ttt caa gaa gcc ttg aag     672
Phe Asn Arg Ala Lys Leu Leu Asn Val Gly Phe Gln Glu Ala Leu Lys
    210                 215                 220 gac tat gac tac acc tgc ttt gtg ttt agt gac gtg gac ctc att cca     720
Asp Tyr Asp Tyr Thr Cys Phe Val Phe Ser Asp Val Asp Leu Ile Pro
225                 230                 235                 240 atg aat gac cat aat gcg tac agg tgt ttt tca cag cca cgg cac att     768
Met Asn Asp His Asn Ala Tyr Arg Cys Phe Ser Gln Pro Arg His Ile
                245                 250                 255 tcc gtt gca atg gat aag ttt gga ttc agc cta cct tat gtt cag tat     816
Ser Val Ala Met Asp Lys Phe Gly Phe Ser Leu Pro Tyr Val Gln Tyr
            260                 265                 270 ttt gga ggt gtc tct gct cta agt aaa caa cag ttt cta acc atc aat     864
Phe Gly Gly Val Ser Ala Leu Ser Lys Gln Gln Phe Leu Thr Ile Asn
        275                 280                 285
```

-continued

```
gga ttt cct aat aat tat tgg ggc tgg gga gga gaa gat gat gac att    912
Gly Phe Pro Asn Asn Tyr Trp Gly Trp Gly Gly Glu Asp Asp Asp Ile
290                 295                 300 ttt aac aga tta gtt ttt aga ggc atg tct ata tct cgc cca aat gct    960
Phe Asn Arg Leu Val Phe Arg Gly Met Ser Ile Ser Arg Pro Asn Ala
305                 310                 315                 320 gtg gtc ggg agg tgt cgc atg atc cgc cac tca aga gac aag aaa aat   1008
Val Val Gly Arg Cys Arg Met Ile Arg His Ser Arg Asp Lys Lys Asn
            325                 330                 335 gaa ccc aat cct cag agg ttt gac cga att gca cac aca aag gag aca   1056
Glu Pro Asn Pro Gln Arg Phe Asp Arg Ile Ala His Thr Lys Glu Thr
            340                 345                 350 atg ctc tct gat ggt ttg aac tca ctc acc tac cag gtg ctg gat gta   1104
Met Leu Ser Asp Gly Leu Asn Ser Leu Thr Tyr Gln Val Leu Asp Val
            355                 360                 365 cag aga tac cca ttg tat acc caa atc aca gtg gac atc ggg aca ccg   1152
Gln Arg Tyr Pro Leu Tyr Thr Gln Ile Thr Val Asp Ile Gly Thr Pro
370                 375                 380 agc tag                                                           1158
Ser
385
```

<210> SEQ ID NO 6
<211> LENGTH: 385
<212> TYPE: PRT
<213> ORGANISM: Homo sapiens

<400> SEQUENCE: 6

```
Met Pro Gly Ala Ser Leu Gln Arg Ala Cys Arg Leu Leu Val Ala Val
  1               5                  10                  15

Cys Ala Leu His Leu Gly Val Thr Leu Val Tyr Tyr Leu Ala Gly Arg
                 20                  25                  30

Asp Leu Ser Arg Leu Pro Gln Leu Val Gly Val Ser Thr Pro Leu Gln
             35                  40                  45

Gly Gly Ser Asn Ser Ala Ala Ile Gly Gln Ser Ser Gly Glu Leu
         50                  55                  60

Arg Thr Gly Gly Ala Arg Pro Pro Pro Leu Gly Ala Ser Ser Gln
 65                  70                  75                  80

Pro Arg Pro Gly Gly Asp Ser Ser Pro Val Val Asp Ser Gly Pro Gly
                 85                  90                  95

Pro Ala Ser Asn Leu Thr Ser Val Pro Val Pro His Thr Thr Ala Leu
            100                 105                 110

Ser Leu Pro Ala Cys Pro Glu Glu Ser Pro Leu Leu Val Gly Pro Met
            115                 120                 125

Leu Ile Glu Phe Asn Met Pro Val Asp Leu Glu Leu Val Ala Lys Gln
        130                 135                 140

Asn Pro Asn Val Lys Met Gly Gly Arg Tyr Ala Pro Arg Asp Cys Val
145                 150                 155                 160

Ser Pro His Lys Val Ala Ile Ile Ile Pro Phe Arg Asn Arg Gln Glu
                165                 170                 175

His Leu Lys Tyr Trp Leu Tyr Tyr Leu His Pro Val Leu Gln Arg Gln
            180                 185                 190

Gln Leu Asp Tyr Gly Ile Tyr Val Ile Asn Gln Ala Gly Asp Thr Ile
        195                 200                 205

Phe Asn Arg Ala Lys Leu Leu Asn Val Gly Phe Gln Glu Ala Leu Lys
210                 215                 220

Asp Tyr Asp Tyr Thr Cys Phe Val Phe Ser Asp Val Asp Leu Ile Pro
```

```
                225                 230                 235                 240
Met Asn Asp His Asn Ala Tyr Arg Cys Phe Ser Gln Pro Arg His Ile
                245                 250                 255

Ser Val Ala Met Asp Lys Phe Gly Phe Ser Leu Pro Tyr Val Gln Tyr
            260                 265                 270

Phe Gly Gly Val Ser Ala Leu Ser Lys Gln Gln Phe Leu Thr Ile Asn
        275                 280                 285

Gly Phe Pro Asn Asn Tyr Trp Gly Trp Gly Gly Glu Asp Asp Asp Ile
    290                 295                 300

Phe Asn Arg Leu Val Phe Arg Gly Met Ser Ile Ser Arg Pro Asn Ala
305                 310                 315                 320

Val Val Gly Arg Cys Arg Met Ile Arg His Ser Arg Asp Lys Lys Asn
                325                 330                 335

Glu Pro Asn Pro Gln Arg Phe Asp Arg Ile Ala His Thr Lys Glu Thr
                340                 345                 350

Met Leu Ser Asp Gly Leu Asn Ser Leu Thr Tyr Gln Val Leu Asp Val
            355                 360                 365

Gln Arg Tyr Pro Leu Tyr Thr Gln Ile Thr Val Asp Ile Gly Thr Pro
    370                 375                 380

Ser
385
```